(12) United States Patent
Phan et al.

(10) Patent No.: US 11,390,867 B2
(45) Date of Patent: Jul. 19, 2022

(54) G-QUADRUPLEX-CONTAINING ANTISENSE OLIGONUCLEOTIDES

(71) Applicant: NANYANG TECHNOLOGICAL UNIVERSITY, Singapore (SG)

(72) Inventors: Anh Tuan Phan, Singapore (SG); Kah Wai Lim, Singapore (SG); Vee Vee Cheong, Singapore (SG); Christopher Brian Henry Jacques Lech, Singapore (SG); Brahim Heddi, Singapore (SG)

(73) Assignee: NANYANG TECHNOLOGICAL UNIVERSITY, Singapore (SG)

( * ) Notice: Subject to any disclaimer, the term of this patent is extended or adjusted under 35 U.S.C. 154(b) by 244 days.

(21) Appl. No.: 16/097,119

(22) PCT Filed: May 2, 2017

(86) PCT No.: PCT/SG2017/050231
§ 371 (c)(1),
(2) Date: Oct. 26, 2018

(87) PCT Pub. No.: WO2017/188898
PCT Pub. Date: Nov. 2, 2017

(65) Prior Publication Data
US 2021/0139893 A1    May 13, 2021

(30) Foreign Application Priority Data
Apr. 29, 2016   (SG) .......................... 10201603451U

(51) Int. Cl.
*C12N 15/113*   (2010.01)

(52) U.S. Cl.
CPC ........ *C12N 15/113* (2013.01); *C12N 2310/11* (2013.01); *C12N 2310/315* (2013.01); *C12N 2310/341* (2013.01); *C12N 2310/3513* (2013.01); *C12N 2310/3515* (2013.01); *C12N 2320/51* (2013.01)

(58) Field of Classification Search
None
See application file for complete search history.

(56) References Cited

U.S. PATENT DOCUMENTS

| | | |
|---|---|---|
| 6,326,199 B1 | 12/2001 | Cook et al. |
| 7,015,315 B1 | 3/2006 | Cook et al. |
| 8,703,728 B2 | 4/2014 | Swayze et al. |
| 8,735,364 B2 | 5/2014 | Crooke et al. |
| 8,912,160 B2 | 12/2014 | Freier et al. |
| 9,045,754 B2 | 6/2015 | Bhanot et al. |
| 9,139,831 B2 | 9/2015 | Crooke et al. |
| 9,163,239 B2 | 10/2015 | Prakash et al. |
| 9,181,549 B2 | 11/2015 | Prakash et al. |
| 9,181,550 B2 | 11/2015 | Prakash et al. |
| 9,249,179 B2 | 2/2016 | Hadwiger et al. |
| 9,359,608 B2 | 6/2016 | Swayze et al. |
| 9,370,582 B2 | 6/2016 | Manoharan et al. |
| 2015/0050738 A1 | 2/2015 | Ozsolak et al. |
| 2015/0368642 A1 | 12/2015 | Albaek et al. |
| 2016/0310519 A1 | 10/2016 | Phan et al. |
| 2016/0376585 A1 | 12/2016 | Manoharan et al. |

FOREIGN PATENT DOCUMENTS

| | | |
|---|---|---|
| EP | 2 463 660 A1 | 6/2012 |
| WO | 99/14226 A2 | 3/1999 |
| WO | 00/66604 A2 | 11/2000 |
| WO | 03/095467 A1 | 11/2003 |
| WO | 2011/002200 A2 | 1/2011 |
| WO | 2012/109395 A1 | 8/2012 |
| WO | 2014/175836 A1 | 10/2014 |
| WO | 2015/153975 A1 | 10/2015 |

OTHER PUBLICATIONS

Bennett et al., "Pharmacology of Antisense Drugs," *Annu. Rev. Pharmacol. Toxicol.*57:81-105, 2017.
Bugaut et al., "Survey and Summary 50'-UTR RNA G-quadruplexes: translation regulation and targeting," *Nucleic Acids Research*, 40(11):4727-4741, 2012.
Crooke et al., "Cellular uptake and trafficking of antisense oligonucleotides," *Nature Biotechnology*, 25(3):230-237. (9 pages).
Crooke, "Molecular Mechanisms of Antisense Oligonucleotides," *Nucleic Acid Therapeutics* 27(2):70-77, 2017. (8 pages).
Eckstein, "Nucleoside Phosphorothioates," *Journal of the American Chemical Society* 88(18):4292-4294, 1966.
Hong et al., "AZD9150, a next-generation antisense oligonucleotide inhibitor of STAT3 with early evidence of clinical activity in lymphoma and lung cancer," *Science Translational Medicine* 7(314), Downloaded from http://stm.sciencemag.org/ on Jan. 7, 2019. (13 pages).
Huppert. "Four-stranded DNA: cancer, gene regulation and drug development," *Phil. Trans. R. Soc. A* 365:2969-2984, 2007.
Khorev et al., "Trivalent, Gal/GalNAc-containing ligands designed for the asialoglycoprotein receptor," *Bioorganic & Medicinal Chemistry* 16:5216-5231, 2008.

(Continued)

*Primary Examiner* — Tracy Vivlemore
(74) *Attorney, Agent, or Firm* — Seed IP Law Group LLP

(57) ABSTRACT

The present invention relates to conjugates comprising (a) an antisense oligonucleotide (ASO) and (b) at least one G-quadruplex structure, wherein the ASO and the at least one G-quadruplex structure are heterologous to each other. The G-quadruplex of the conjugate may be further conjugated with ligands or functional moieties for addressable delivery and enhanced properties including potency and therapeutic index. Further encompassed are such conjugates for use as a medicament, a method of modulating the stability, translation, splicing, cleavage, or activity of a target nucleic acid molecule using such conjugates, and use of G-quadruplex in stabilizing antisense oligonucleotides.

19 Claims, 10 Drawing Sheets
Specification includes a Sequence Listing.

(56) References Cited

OTHER PUBLICATIONS

Koshkin et al., "LNA (Locked Nucleic Acids): Synthesis of the Adenine, Cytosine, Guanine, 5-Methylcytosine, Thymine and Uracil Bicyclonucleoside Monomers, Oligomerisation, and Unprecedented Nucleic Acid Recognition," *Tetrahedron 54*:3607-3630, 1998.

Loh et al., "DNA G-Quadruplex as a Reporter System for Sensor Development," Nucleic Acids—From Basic Aspects to Laboratory Tools Downloaded from: http://www.intechopen.com/books/nucleic-acids-from-basicaspects-to-laboratory-tools, 2016. (17 pages).

Lönn et al., "Enhancing Endosomal Escape for Intracellular Delivery of Macromolecular Biologic Therapeutics," *Scientific Reports 6*:32301, 2016. (10 pages).

Matsuda et al., "siRNA Conjugates Carrying Sequentially Assembled Trivalent N-Acetylgalactosamine Linked Through Nucleosides Elicit Robust Gene Silencing In Vivo in Hepatocytes," *ACS Chem. Biol. 10*:1181-1187, 2015.

Matteucci et al., "Synthesis of Deoxyoligonucleotides on a Polymer Support," *J. Am. Chem. Soc. 103*:3185-3191, 1981.

Monia et al., "Evaluation of 2'-Modified Oligonucleotides Containing 2'-Deoxy Gaps as Antisense Inhibitors of Gene Expression," *The Journal of Biological Chemistry*, 268(19):14514-14522, 1993.

Nair et al., "Multivalent N-Acetylgalactosamine-Conjugated siRNA Localizes in Hepatocytes and Elicits Robust RNAi-Mediated Gene Silencing," *J. Am. Chem. Soc. 136*:16958-16961, 2014.

Obika et al., "Synthesis of 2'-O,4'-C-Methyleneuridine and -cytidine. Novel Bicyclic Nucleosides Having a Fixed $C_3$,-endo Sugar Puckering," *Tetrahedron Letters*, 38(50):8735-8738, 1997.

Phan et al., "Human telomeric G-quadruplex: structures of DNA and RNA sequences," *FEBS Journal 277*:1107-1117, 2010.

Prakash et al., "Targeted delivery of antisense oligonucleotides to hepatocytes using triantennary N-acetyl galactosamine improves potency 10-fold in mice," *Nucleic Acids Research 42*(13):8796-8807, 2014.

Rajeev et al., "Hepatocyte-Specific Delivery of siRNAs Conjugated to Novel Non-nucleosidic Trivalent N-Acetylgalactosamine Elicits Robust Gene Silencing in Vivo," *ChemBioChem 16*:903-908, 2015.

Rhodes et al., "G-quadruplexes and their regulatory roles in biology," *Nucleic Acids Research 43*(18):8627-8637, 2015.

Rozema et al., "Dynamic PolyConjugates for targeted in vivo delivery of siRNA to hepatocytes," *PNAS 104*(32):12982-12987, 2007.

Sagi, "G-quadruplexes incorporating modified constituents: a review," *Journal of Biomolecular Structure and Dynamics*, 32(3):477-511, 2014.

Seth et al., "Short Antisense Oligonucleotides with Novel 2'-4' Conformationaly Restricted Nucleoside Analogues Show Improved Potency without Increased Toxicity in Animals," *J. Med. Chem. 52*:10-13, 2009.

Sharma et al., "Oligonucleotide therapeutics: chemistry, delivery and clinical progress," *Future Med. Chem. 7*(16):2221-2242, 2015.

Sliedregt et al., "Design and Synthesis of Novel Amphiphilic Dendritic Galactosides for Selective Targeting of Liposomes to the Hepatic Asialoglycoprotein Receptor," *J. Med. Chem. 42*:609-618, 1999.

Stephenson et al., "Inhibition of Rous sarcoma Viral RNA translation by a Specific Oligodeoxyribonucleotide," *Proc. Natl. Acad. Sci. 75*(1):285-288, 1978. (5 pages).

Straarup et al., "Short locked nucleic acid antisense oligonucleotides potently reduce apolipoprotein B mRNA and serum cholesterol in mice and non-human primates," *Nucleic Acids Research 38*(20):7100-7111, 2010.

Winkler, "Oligonucleotide conjugates for therapeutic applications," *Ther Deliv. 4*(7):791-809, 2013. (29 pages).

Zamecnik et al., "Inhibition of Rous sarcoma Virus Replication and Cell Specific Oligodeoxynucleotide," *Proc. Natl. Acad. Sci. 75*(1):280-284, 1978. (6 pages).

Extended European Search Report corresponding to related EP Application No. 17790026.3, (five pages), dated Aug. 27, 2019.

Figure 2-I
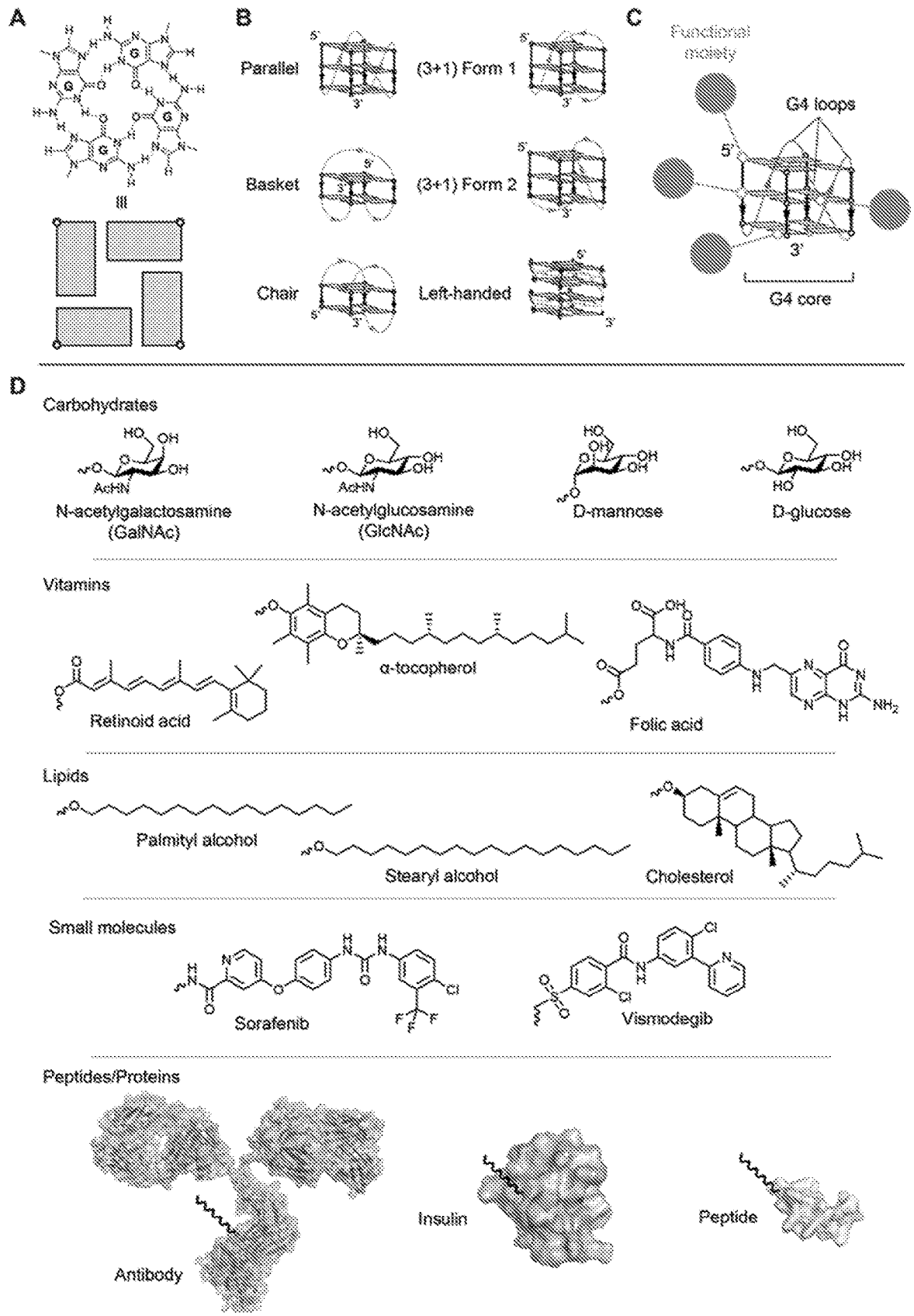

Figure 2-II
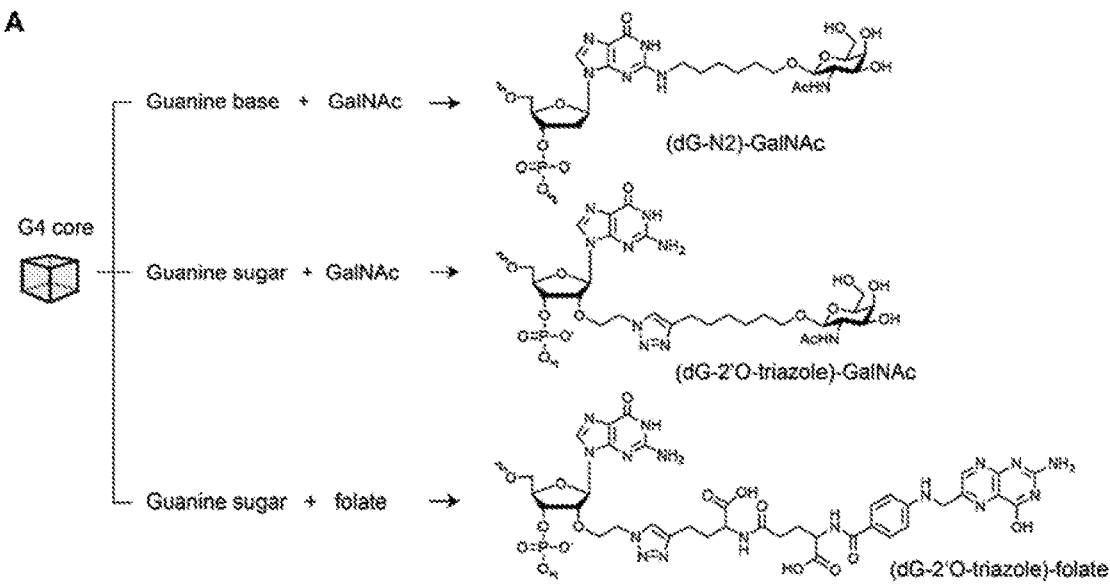
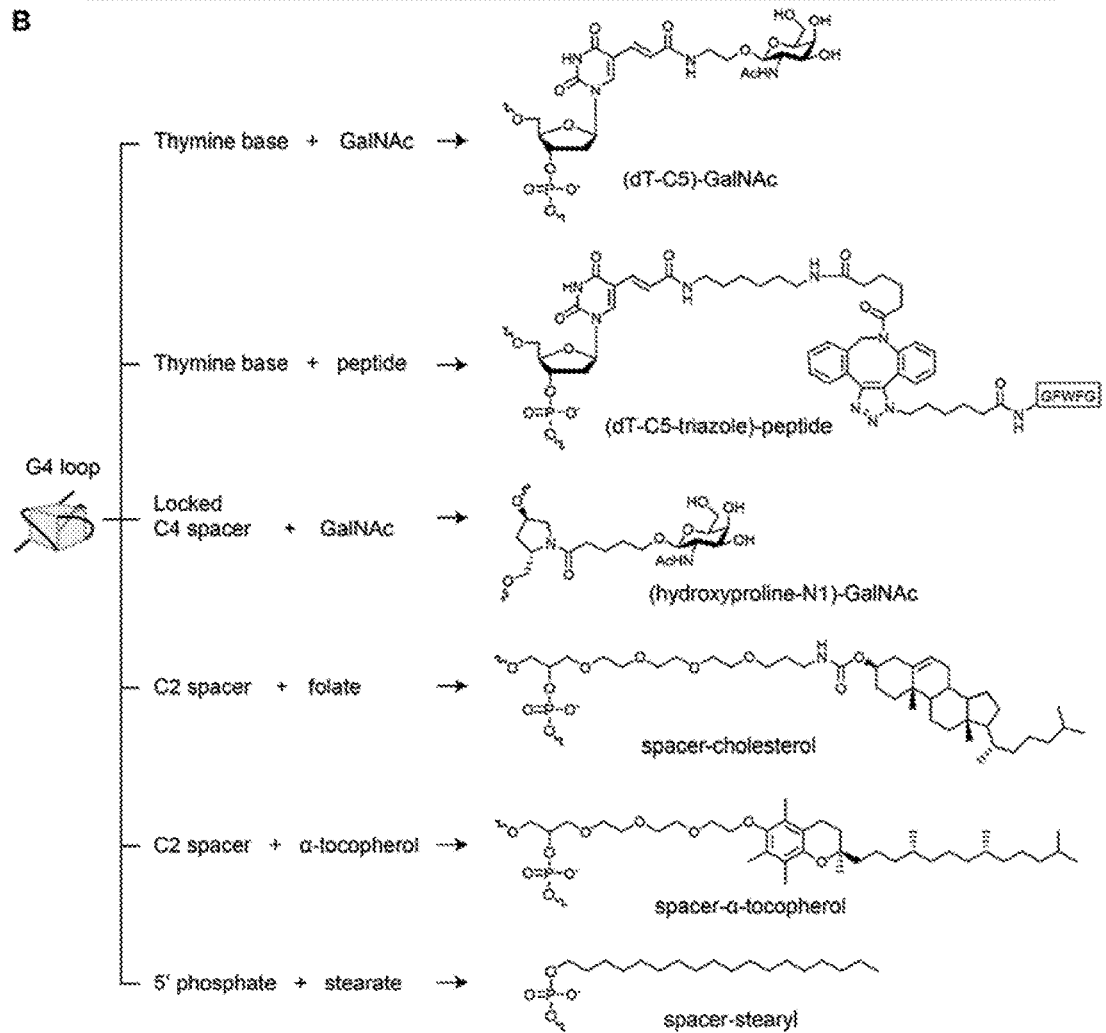

Figure 3-I
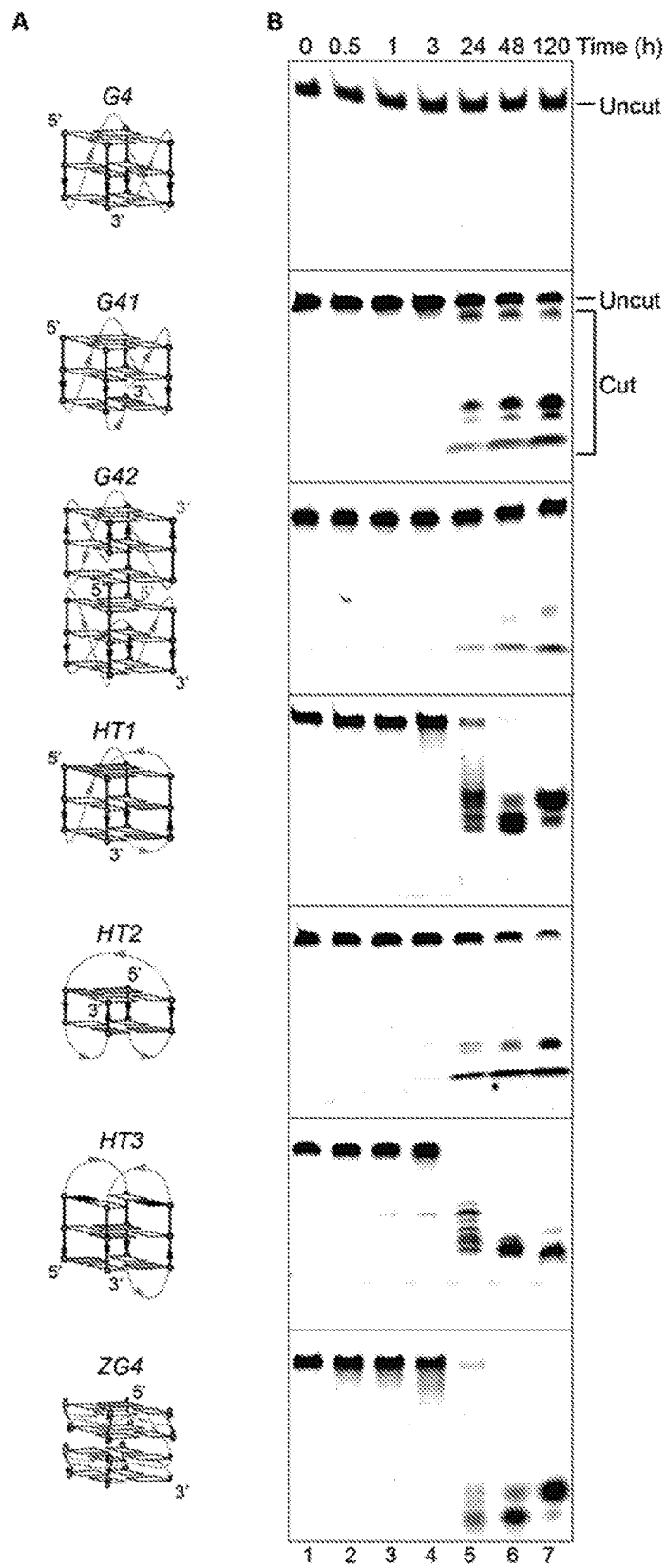

Figure 3-II
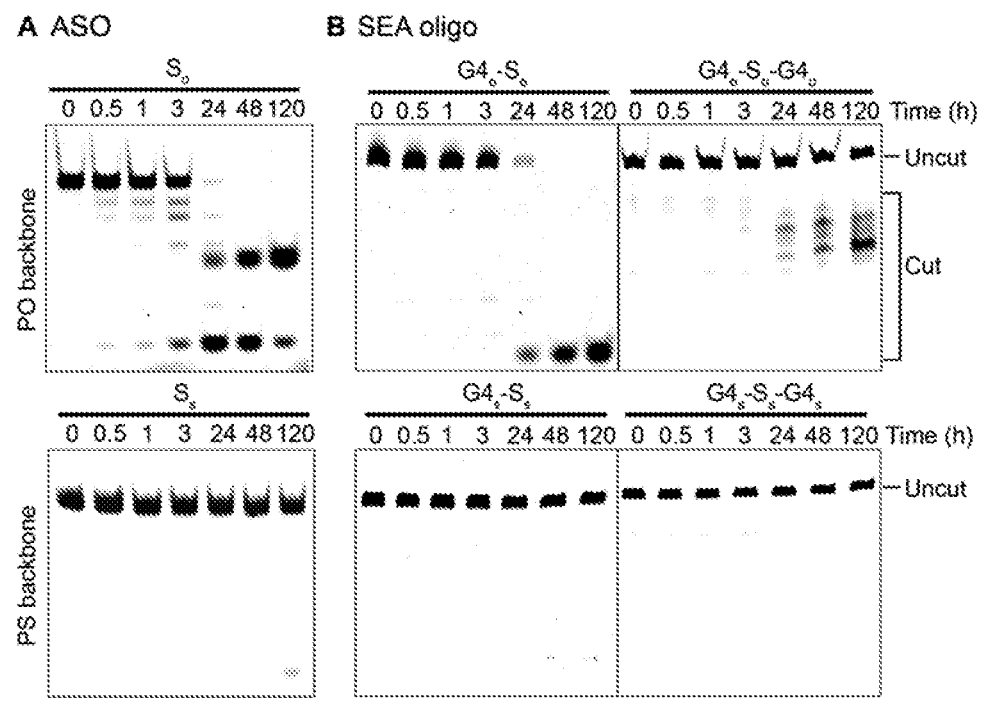

Figure 4-I
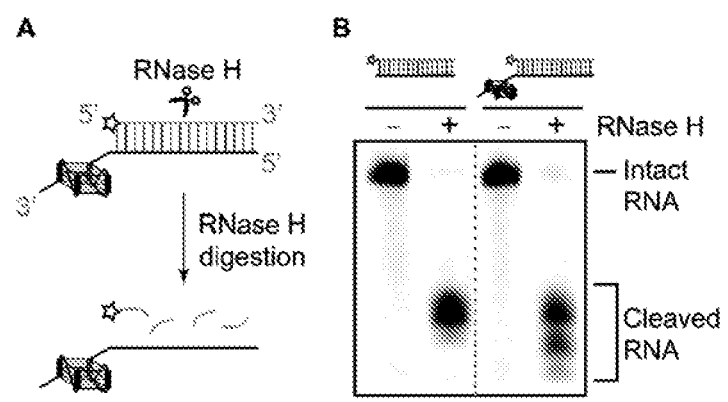

Figure 4-II
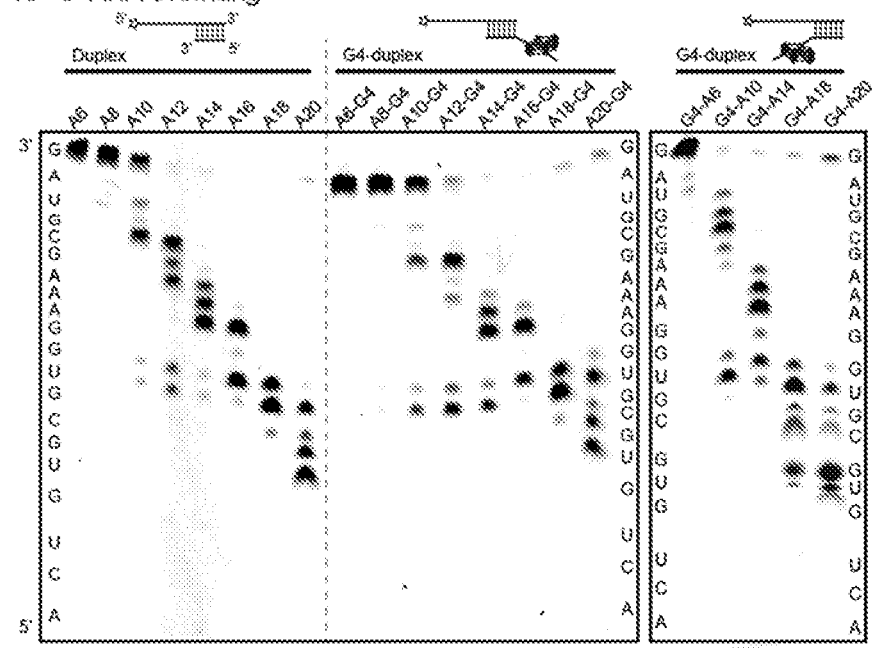
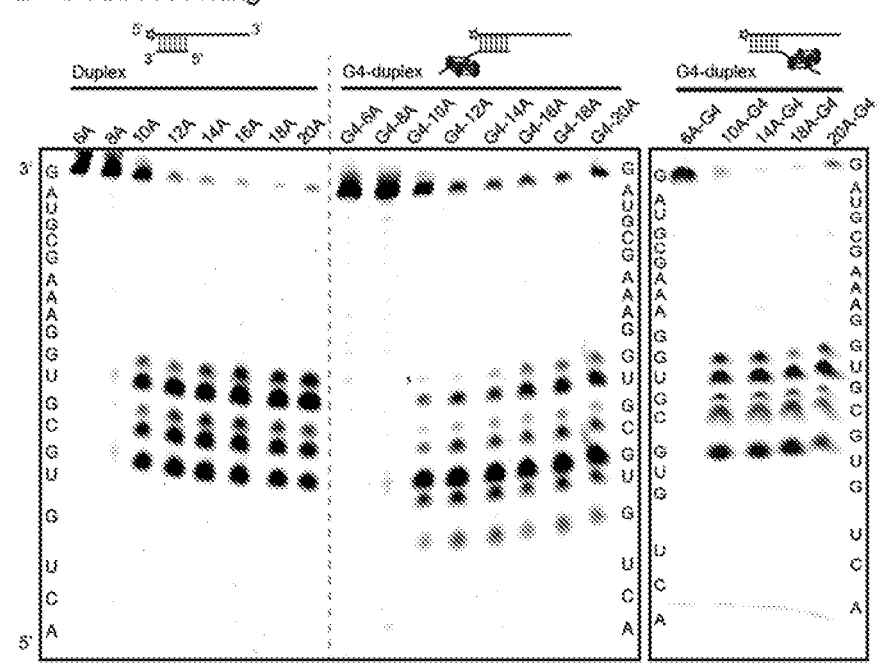

Figure 4-III
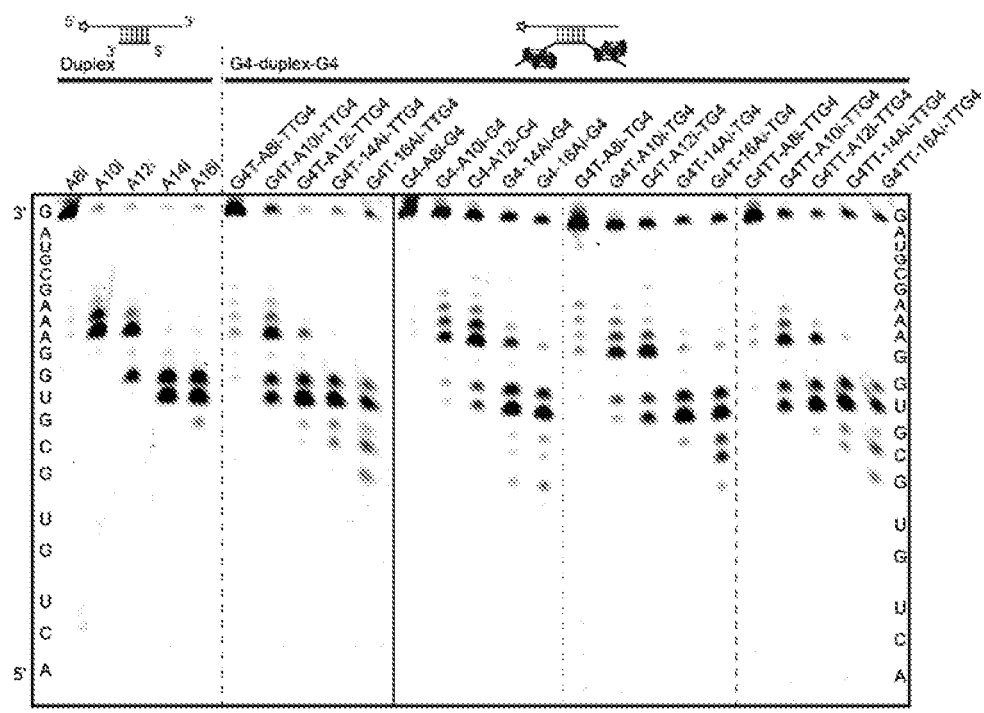

Figure 7-I
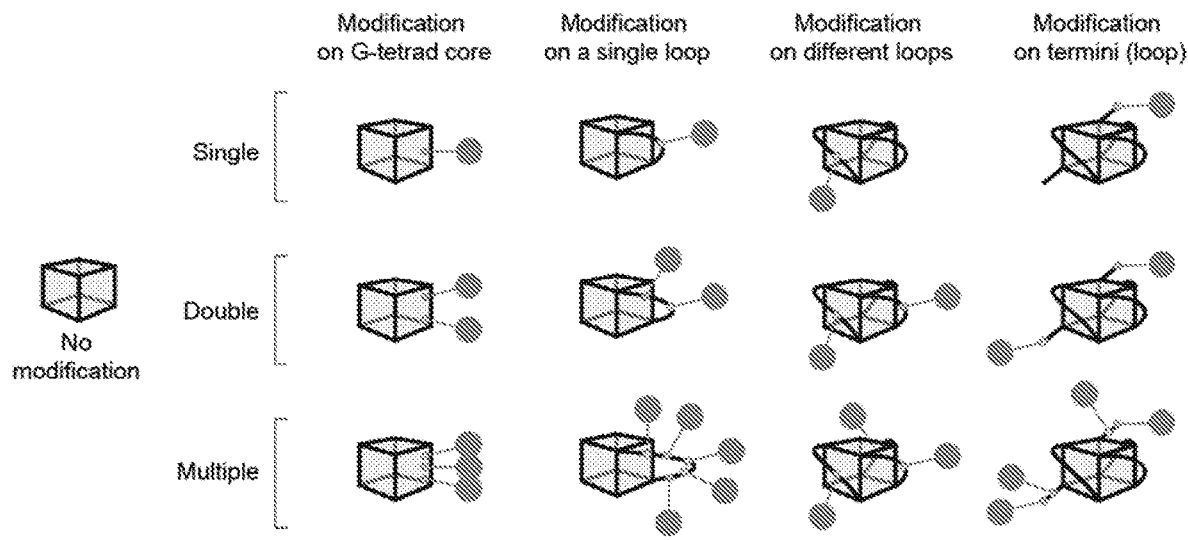
Figure 7-II
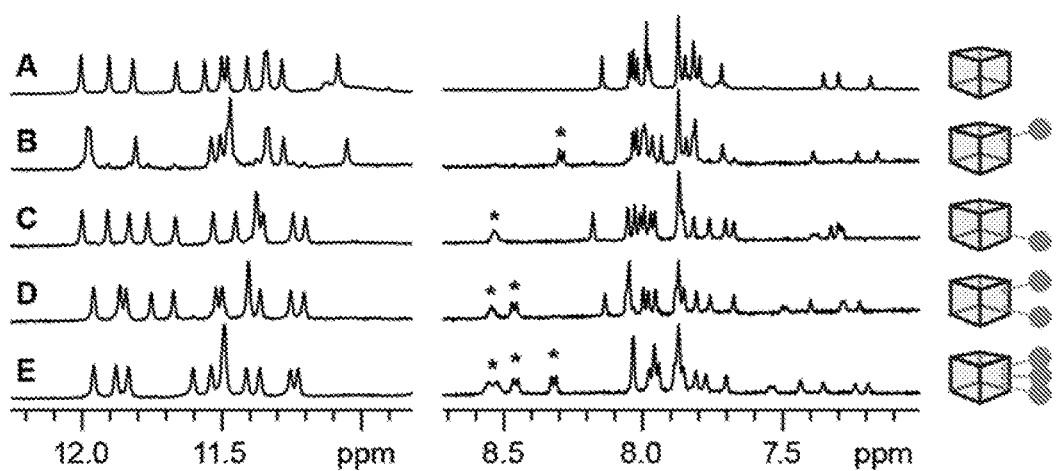

SEQUENCE LISTING

```
<160> NUMBER OF SEQ ID NOS: 98

<210> SEQ ID NO 1
<211> LENGTH: 15
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (15)..(15)
<223> OTHER INFORMATION: n is C conjugated to 6-FAM.

<400> SEQUENCE: 1
aacacgtcta tacgn                                                          15

<210> SEQ ID NO 2
<211> LENGTH: 15
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(15)
<223> OTHER INFORMATION: phosphorothioate backbone
<220> FEATURE:
<221> NAME/KEY: misc_feature
<222> LOCATION: (15)..(15)
<223> OTHER INFORMATION: n is c conjugated to 6-FAM

<400> SEQUENCE: 2
aacacgtcta tacgn                                                          15

<210> SEQ ID NO 3
<211> LENGTH: 18
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (18)..(18)
<223> OTHER INFORMATION: n is T conjugated to 6-FAM

<400> SEQUENCE: 3
ttgggtgggt gggtgggn                                                       18

<210> SEQ ID NO 4
<211> LENGTH: 24
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is T conjugated to 6-FAM
```

<400> SEQUENCE: 4
ngagggtggt gagggtgggg aagg                                          24

<210> SEQ ID NO 5
<211> LENGTH: 16
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (16)..(16)
<223> OTHER INFORMATION: n is t conjugated to 6-FAM

<400> SEQUENCE: 5
ggggtgggag gagggn                                                   16

<210> SEQ ID NO 6
<211> LENGTH: 24
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is T conjugated to 6-FAM

<400> SEQUENCE: 6
ntgggttagg gttagggtta ggga                                          24

<210> SEQ ID NO 7
<211> LENGTH: 22
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (22)..(22)
<223> OTHER INFORMATION: n is T conjugated to 6-FAM

<400> SEQUENCE: 7
gggttagggt tagggttagg gn                                            22

<210> SEQ ID NO 8
<211> LENGTH: 22
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<223> OTHER INFORMATION: n is A conjugated to 6-FAM
<220> FEATURE:
<221> NAME/KEY: misc_feature
<222> LOCATION: (1)..(1)
<223> OTHER INFORMATION: n is a, c, g, or t

<400> SEQUENCE: 8
ngggctaggg ctagggctag gg                                            22

<210> SEQ ID NO 9
<211> LENGTH: 28
<212> TYPE: DNA
<213> ORGANISM: artificial sequence
<220> FEATURE:
<223> OTHER INFORMATION: synthetic sequence

```
<220> FEATURE:
<221> NAME/KEY: misc_feature
<222> LOCATION: (28)..(28)
<223> OTHER INFORMATION: n is T conjugated 6-FAM

<400> SEQUENCE: 9
tggtggtggt ggttgtggtg gtggtgtn                                              28

<210> SEQ ID NO 10
<211> LENGTH: 33
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (33)..(33)
<223> OTHER INFORMATION: n is C conjugated to 6-FAM

<400> SEQUENCE: 10
ttgggtgggt gggtgggtaa cacgtctata cgn                                        33

<210> SEQ ID NO 11
<211> LENGTH: 33
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(33)
<223> OTHER INFORMATION: phosphorothioate backbone
<220> FEATURE:
<221> NAME/KEY: misc_feature
<222> LOCATION: (33)..(33)
<223> OTHER INFORMATION: n is C conjugated to 6-FAM

<400> SEQUENCE: 11
ttgggtgggt gggtgggtaa cacgtctata cgn                                        33

<210> SEQ ID NO 12
<211> LENGTH: 50
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (50)..(50)
<223> OTHER INFORMATION: n is T conjugated to 6-FAM

<400> SEQUENCE: 12
ttgggtgggt gggtgggtaa cacgtctata cgctgggtgg gtgggtgggn                      50

<210> SEQ ID NO 13
<211> LENGTH: 50
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(50)
<223> OTHER INFORMATION: phosphorothioate backbone
<220> FEATURE:
<221> NAME/KEY: misc_feature
<222> LOCATION: (50)..(50)
<223> OTHER INFORMATION: n is T conjugated to 6-FAM

<400> SEQUENCE: 13
```

```
ttgggtgggt gggtgggtaa cacgtctata cgctgggtgg gtgggtgggn    50
```

```
<210> SEQ ID NO 14
<211> LENGTH: 20
<212> TYPE: RNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is A conjugated to 6-FAM

<400> SEQUENCE: 14
```

```
ncugugcgug gaaagcguag                                    20
```

```
<210> SEQ ID NO 15
<211> LENGTH: 6
<212> TYPE: DNA
<213> ORGANISM: artificial sequence
<220> FEATURE:
<223> OTHER INFORMATION: synthetic sequence

<400> SEQUENCE: 15
```

```
ctacgc                                                    6
```

```
<210> SEQ ID NO 16
<211> LENGTH: 8
<212> TYPE: DNA
<213> ORGANISM: artificial sequence
<220> FEATURE:
<223> OTHER INFORMATION: synthetic sequenc

<400> SEQUENCE: 16
```

```
ctacgctt                                                  8
```

```
<210> SEQ ID NO 17
<211> LENGTH: 10
<212> TYPE: DNA
<213> ORGANISM: artificial sequence
<220> FEATURE:
<223> OTHER INFORMATION: synthetic sequence

<400> SEQUENCE: 17
```

```
ctacgctttc                                               10
```

```
<210> SEQ ID NO 18
<211> LENGTH: 12
<212> TYPE: DNA
<213> ORGANISM: artificial sequence
<220> FEATURE:
<223> OTHER INFORMATION: synthetic sequence

<400> SEQUENCE: 18
```

```
ctacgctttc ca                                            12
```

```
<210> SEQ ID NO 19
<211> LENGTH: 14
<212> TYPE: DNA
<213> ORGANISM: artificial sequence
<220> FEATURE:
<223> OTHER INFORMATION: synthetic sequence

<400> SEQUENCE: 19
```

```
ctacgctttc cacg                                          14
```

-continued

```
<210> SEQ ID NO 20
<211> LENGTH: 16
<212> TYPE: DNA
<213> ORGANISM: artificial sequence
<220> FEATURE:
<223> OTHER INFORMATION: synthetic sequence

<400> SEQUENCE: 20
ctacgctttc cacgca                                                       16

<210> SEQ ID NO 21
<211> LENGTH: 18
<212> TYPE: DNA
<213> ORGANISM: artificial sequence
<220> FEATURE:
<223> OTHER INFORMATION: synthetic sequence

<400> SEQUENCE: 21
ctacgctttc cacgcaca                                                     18

<210> SEQ ID NO 22
<211> LENGTH: 20
<212> TYPE: DNA
<213> ORGANISM: artificial sequence
<220> FEATURE:
<223> OTHER INFORMATION: synthetic sequence

<400> SEQUENCE: 22
ctacgctttc cacgcacagt                                                   20

<210> SEQ ID NO 23
<211> LENGTH: 6
<212> TYPE: DNA
<213> ORGANISM: artificial sequence
<220> FEATURE:
<223> OTHER INFORMATION: synthetic sequence

<400> SEQUENCE: 23 cacagt                                                                   6

<210> SEQ ID NO 24
<211> LENGTH: 8
<212> TYPE: DNA
<213> ORGANISM: artificial sequence
<220> FEATURE:
<223> OTHER INFORMATION: synthetic sequence

<400> SEQUENCE: 24 cgcacagt                                                                 8

<210> SEQ ID NO 25
<211> LENGTH: 10
<212> TYPE: DNA
<213> ORGANISM: artificial sequence
<220> FEATURE:
<223> OTHER INFORMATION: synthetic sequence

<400> SEQUENCE: 25
cacgcacagt                                                              10

<210> SEQ ID NO 26
<211> LENGTH: 12
<212> TYPE: DNA
<213> ORGANISM: artificial sequence
<220> FEATURE:
<223> OTHER INFORMATION: synthetic sequence
```

```
<400> SEQUENCE: 26
tccacgcaca gt                                                    12

<210> SEQ ID NO 27
<211> LENGTH: 14
<212> TYPE: DNA
<213> ORGANISM: artificial sequence
<220> FEATURE:
<223> OTHER INFORMATION: synthetic sequence

<400> SEQUENCE: 27
tttccacgca cagt                                                  14

<210> SEQ ID NO 28
<211> LENGTH: 16
<212> TYPE: DNA
<213> ORGANISM: artificial sequence
<220> FEATURE:
<223> OTHER INFORMATION: synthetic sequence

<400> SEQUENCE: 28
gctttccacg cacagt                                                16

<210> SEQ ID NO 29
<211> LENGTH: 18
<212> TYPE: DNA
<213> ORGANISM: artificial sequence
<220> FEATURE:
<223> OTHER INFORMATION: synthetic sequence

<400> SEQUENCE: 29
acgctttcca cgcacagt                                              18

<210> SEQ ID NO 30
<211> LENGTH: 20
<212> TYPE: DNA
<213> ORGANISM: artificial sequence
<220> FEATURE:
<223> OTHER INFORMATION: synthetic sequence

<400> SEQUENCE: 30
ctacgctttc cacgcacagt                                            20

<210> SEQ ID NO 31
<211> LENGTH: 8
<212> TYPE: DNA
<213> ORGANISM: artificial sequence
<220> FEATURE:
<223> OTHER INFORMATION: synthetic sequence

<400> SEQUENCE: 31 tttccacg                                                          8

<210> SEQ ID NO 32
<211> LENGTH: 10
<212> TYPE: DNA
<213> ORGANISM: artificial sequence
<220> FEATURE:
<223> OTHER INFORMATION: synthetic sequence

<400> SEQUENCE: 32
ctttccacgc                                                       10

<210> SEQ ID NO 33
<211> LENGTH: 12
```

```
<212> TYPE: DNA
<213> ORGANISM: artificial sequence
<220> FEATURE:
<223> OTHER INFORMATION: synthetic sequence

<400> SEQUENCE: 33
gctttccacg ca                                                      12

<210> SEQ ID NO 34
<211> LENGTH: 14
<212> TYPE: DNA
<213> ORGANISM: artificial sequence
<220> FEATURE:
<223> OTHER INFORMATION: synthetic sequence

<400> SEQUENCE: 34
cgctttccac gcac                                                    14

<210> SEQ ID NO 35
<211> LENGTH: 16
<212> TYPE: DNA
<213> ORGANISM: artificial sequence
<220> FEATURE:
<223> OTHER INFORMATION: synthetic sequence

<400> SEQUENCE: 35
acgctttcca cgcaca                                                  16

<210> SEQ ID NO 36
<211> LENGTH: 25
<212> TYPE: DNA
<213> ORGANISM: artificial sequence
<220> FEATURE:
<223> OTHER INFORMATION: synthetic sequence

<400> SEQUENCE: 36
ttgggtgggt gggtgggttc tacgc                                        25

<210> SEQ ID NO 37
<211> LENGTH: 27
<212> TYPE: DNA
<213> ORGANISM: artificial sequence
<220> FEATURE:
<223> OTHER INFORMATION: synthetic sequence

<400> SEQUENCE: 37
ttgggtgggt gggtgggttc tacgctt                                      27

<210> SEQ ID NO 38
<211> LENGTH: 29
<212> TYPE: DNA
<213> ORGANISM: artificial sequence
<220> FEATURE:
<223> OTHER INFORMATION: synthetic sequence

<400> SEQUENCE: 38
ttgggtgggt gggtgggttc tacgctttc                                    29

<210> SEQ ID NO 39
<211> LENGTH: 31
<212> TYPE: DNA
<213> ORGANISM: artificial sequence
<220> FEATURE:
<223> OTHER INFORMATION: synthetic sequence

<400> SEQUENCE: 39
```
ttgggtgggt gggtgggttc tacgctttcc a        31

<210> SEQ ID NO 40
<211> LENGTH: 33
<212> TYPE: DNA
<213> ORGANISM: artificial sequence
<220> FEATURE:
<223> OTHER INFORMATION: synthetic sequence

<400> SEQUENCE: 40
ttgggtgggt gggtgggttc tacgctttcc acg       33

<210> SEQ ID NO 41
<211> LENGTH: 35
<212> TYPE: DNA
<213> ORGANISM: artificial sequence
<220> FEATURE:
<223> OTHER INFORMATION: synthetic sequence

<400> SEQUENCE: 41
ttgggtgggt gggtgggttc tacgctttcc acgca     35

<210> SEQ ID NO 42
<211> LENGTH: 37
<212> TYPE: DNA
<213> ORGANISM: artificial sequence
<220> FEATURE:
<223> OTHER INFORMATION: synthetic sequence

<400> SEQUENCE: 42
ttgggtgggt gggtgggttc tacgctttcc acgcaca   37

<210> SEQ ID NO 43
<211> LENGTH: 39
<212> TYPE: DNA
<213> ORGANISM: artificial sequence
<220> FEATURE:
<223> OTHER INFORMATION: synthetic sequence

<400> SEQUENCE: 43
ttgggtgggt gggtgggttc tacgctttcc acgcacagt 39

<210> SEQ ID NO 44
<211> LENGTH: 25
<212> TYPE: DNA
<213> ORGANISM: artificial sequence
<220> FEATURE:
<223> OTHER INFORMATION: synthetic sequence

<400> SEQUENCE: 44
cacagtttgg gtgggtgggt gggtt               25

<210> SEQ ID NO 45
<211> LENGTH: 27
<212> TYPE: DNA
<213> ORGANISM: artificial sequence
<220> FEATURE:
<223> OTHER INFORMATION: synthetic sequence

<400> SEQUENCE: 45
cgcacagttt gggtgggtgg gtgggtt             27

<210> SEQ ID NO 46
<211> LENGTH: 29
<212> TYPE: DNA
<213> ORGANISM: artificial sequence

```
<220> FEATURE:
<223> OTHER INFORMATION: synthetic sequence

<400> SEQUENCE: 46
cacgcacagt ttgggtgggt gggtgggtt                                          29

<210> SEQ ID NO 47
<211> LENGTH: 31
<212> TYPE: DNA
<213> ORGANISM: artificial sequence
<220> FEATURE:
<223> OTHER INFORMATION: synthetic sequence

<400> SEQUENCE: 47
tccacgcaca gtttgggtgg gtgggtgggt t                                       31

<210> SEQ ID NO 48
<211> LENGTH: 33
<212> TYPE: DNA
<213> ORGANISM: artificial sequence
<220> FEATURE:
<223> OTHER INFORMATION: synthetic sequence

<400> SEQUENCE: 48
tttccacgca cagtttgggt gggtgggtgg gtt                                     33

<210> SEQ ID NO 49
<211> LENGTH: 35
<212> TYPE: DNA
<213> ORGANISM: artificial sequence
<220> FEATURE:
<223> OTHER INFORMATION: synthetic sequee

<400> SEQUENCE: 49
gctttccacg cacagtttgg gtgggtgggt gggtt                                   35

<210> SEQ ID NO 50
<211> LENGTH: 37
<212> TYPE: DNA
<213> ORGANISM: artificial sequence
<220> FEATURE:
<223> OTHER INFORMATION: synthetic sequence

<400> SEQUENCE: 50
acgctttcca cgcacagttt gggtgggtgg gtgggtt                                 37

<210> SEQ ID NO 51
<211> LENGTH: 39
<212> TYPE: DNA
<213> ORGANISM: artificial sequence
<220> FEATURE:
<223> OTHER INFORMATION: synthetic sequence

<400> SEQUENCE: 51
ctacgctttc cacgcacagt ttgggtgggt gggtgggtt                               39

<210> SEQ ID NO 52
<211> LENGTH: 25
<212> TYPE: DNA
<213> ORGANISM: artificial sequence
<220> FEATURE:
<223> OTHER INFORMATION: synthetic sequence

<400> SEQUENCE: 52
ctacgcttgg gtgggtgggt gggtt                                              25
```

<210> SEQ ID NO 53
<211> LENGTH: 29
<212> TYPE: DNA
<213> ORGANISM: artificial sequence
<220> FEATURE:
<223> OTHER INFORMATION: synthetic sequence

<400> SEQUENCE: 53
ctacgctttc ttgggtgggt gggtgggtt                                      29

<210> SEQ ID NO 54
<211> LENGTH: 33
<212> TYPE: DNA
<213> ORGANISM: artificial sequence
<220> FEATURE:
<223> OTHER INFORMATION: synthetic sequence

<400> SEQUENCE: 54
ctacgctttc cacgttgggt gggtgggtgg gtt                                 33

<210> SEQ ID NO 55
<211> LENGTH: 37
<212> TYPE: DNA
<213> ORGANISM: artificial sequence
<220> FEATURE:
<223> OTHER INFORMATION: synthetic sequence

<400> SEQUENCE: 55
ctacgctttc cacgcacatt gggtgggtgg gtgggtt                             37

<210> SEQ ID NO 56
<211> LENGTH: 39
<212> TYPE: DNA
<213> ORGANISM: artificial sequence
<220> FEATURE:
<223> OTHER INFORMATION: synthetic sequence

<400> SEQUENCE: 56
ctacgctttc cacgcacagt tgggtgggt gggtgggtt                            39

<210> SEQ ID NO 57
<211> LENGTH: 25
<212> TYPE: DNA
<213> ORGANISM: artificial sequence
<220> FEATURE:
<223> OTHER INFORMATION: synthetic sequence

<400> SEQUENCE: 57
ttgggtgggt gggtgggttc acagt                                         25

<210> SEQ ID NO 58
<211> LENGTH: 29
<212> TYPE: DNA
<213> ORGANISM: artificial sequence
<220> FEATURE:
<223> OTHER INFORMATION: synthetic sequence

<400> SEQUENCE: 58
ttgggtgggt gggtgggttc acgcacagt                                     29

<210> SEQ ID NO 59
<211> LENGTH: 33
<212> TYPE: DNA
<213> ORGANISM: artificial sequence
<220> FEATURE:
<223> OTHER INFORMATION: synthetic sequence

```
<400> SEQUENCE: 59
ttgggtgggt gggtgggttt ttccacgcac agt                          33

<210> SEQ ID NO 60
<211> LENGTH: 37
<212> TYPE: DNA
<213> ORGANISM: artificial sequence
<220> FEATURE:
<223> OTHER INFORMATION: synthetic sequence

<400> SEQUENCE: 60
ttgggtgggt gggtgggtta cgctttccac gcacagt                      37

<210> SEQ ID NO 61
<211> LENGTH: 39
<212> TYPE: DNA
<213> ORGANISM: artificial sequence
<220> FEATURE:
<223> OTHER INFORMATION: synthetic sequence

<400> SEQUENCE: 61
ttgggtgggt gggtgggttc tacgctttcc acgcacagt                    39

<210> SEQ ID NO 62
<211> LENGTH: 44
<212> TYPE: DNA
<213> ORGANISM: artificial sequence
<220> FEATURE:
<223> OTHER INFORMATION: synthetic sequence

<400> SEQUENCE: 62
ttgggtgggt gggtgggttt tccacgttgg gtgggtgggt gggt              44

<210> SEQ ID NO 63
<211> LENGTH: 46
<212> TYPE: DNA
<213> ORGANISM: artificial sequence
<220> FEATURE:
<223> OTHER INFORMATION: synthetic sequence

<400> SEQUENCE: 63
ttgggtgggt gggtgggtct ttccacgctt gggtgggtgg gtgggt            46

<210> SEQ ID NO 64
<211> LENGTH: 48
<212> TYPE: DNA
<213> ORGANISM: artificial sequence
<220> FEATURE:
<223> OTHER INFORMATION: synthetic sequence

<400> SEQUENCE: 64
ttgggtgggt gggtgggtgc tttccacgca ttgggtgggt gggtgggt          48

<210> SEQ ID NO 65
<211> LENGTH: 50
<212> TYPE: DNA
<213> ORGANISM: artificial sequence
<220> FEATURE:
<223> OTHER INFORMATION: synthetic sequence

<400> SEQUENCE: 65
ttgggtgggt gggtgggtcg ctttccacgc acttgggtgg gtgggtgggt        50

<210> SEQ ID NO 66
```

<210> SEQ ID NO 66
<211> LENGTH: 52
<212> TYPE: DNA
<213> ORGANISM: artificial sequence
<220> FEATURE:
<223> OTHER INFORMATION: synthetic sequence

<400> SEQUENCE: 66
ttgggtgggt gggtgggtac gctttccacg cacattgggt gggtgggtgg gt           52

<210> SEQ ID NO 67
<211> LENGTH: 41
<212> TYPE: DNA
<213> ORGANISM: artificial sequence
<220> FEATURE:
<223> OTHER INFORMATION: synthetic sequence

<400> SEQUENCE: 67
ttgggtgggt gggtgggttt ccacggggtg ggtgggtggg t                       41

<210> SEQ ID NO 68
<211> LENGTH: 43
<212> TYPE: DNA
<213> ORGANISM: artificial sequence
<220> FEATURE:
<223> OTHER INFORMATION: synthetic sequence

<400> SEQUENCE: 68
ttgggtgggt gggtgggctt tccacgcggg tgggtgggtg ggt                     43

<210> SEQ ID NO 69
<211> LENGTH: 45
<212> TYPE: DNA
<213> ORGANISM: artificial sequence
<220> FEATURE:
<223> OTHER INFORMATION: synthetic sequence

<400> SEQUENCE: 69
ttgggtgggt gggtggggct ttccacgcag ggtgggtggg tgggt                   45

<210> SEQ ID NO 70
<211> LENGTH: 47
<212> TYPE: DNA
<213> ORGANISM: artificial sequence
<220> FEATURE:
<223> OTHER INFORMATION: synthetic sequence

<400> SEQUENCE: 70
ttgggtgggt gggtgggcgc tttccacgca cgggtgggtg ggtgggt                 47

<210> SEQ ID NO 71
<211> LENGTH: 49
<212> TYPE: DNA
<213> ORGANISM: artificial sequence
<220> FEATURE:
<223> OTHER INFORMATION: synthetic sequence

<400> SEQUENCE: 71
ttgggtgggt gggtgggacg ctttccacgc acagggtggg tgggtgggt               49

<210> SEQ ID NO 72
<211> LENGTH: 43
<212> TYPE: DNA
<213> ORGANISM: artificial sequence
<220> FEATURE:
<223> OTHER INFORMATION: synthetic sequence

<400> SEQUENCE: 72

```
ttgggtgggt gggtgggttt tccacgtggg tgggtgggtg ggt            43
```

<210> SEQ ID NO 73
<211> LENGTH: 45
<212> TYPE: DNA
<213> ORGANISM: artificial sequence
<220> FEATURE:
<223> OTHER INFORMATION: synthetic sequence

<400> SEQUENCE: 73

```
ttgggtgggt gggtgggtct ttccacgctg ggtgggtggg tgggt          45
```

<210> SEQ ID NO 74
<211> LENGTH: 47
<212> TYPE: DNA
<213> ORGANISM: artificial sequence
<220> FEATURE:
<223> OTHER INFORMATION: synthetic sequence

<400> SEQUENCE: 74

```
ttgggtgggt gggtgggtgc tttccacgca tgggtgggtg ggtgggt        47
```

<210> SEQ ID NO 75
<211> LENGTH: 49
<212> TYPE: DNA
<213> ORGANISM: artificial sequence
<220> FEATURE:
<223> OTHER INFORMATION: synthetic sequence

<400> SEQUENCE: 75

```
ttgggtgggt gggtgggtcg ctttccacgc actgggtggg tgggtgggt      49
```

<210> SEQ ID NO 76
<211> LENGTH: 51
<212> TYPE: DNA
<213> ORGANISM: artificial sequence
<220> FEATURE:
<223> OTHER INFORMATION: synthetic sequence

<400> SEQUENCE: 76

```
ttgggtgggt gggtgggtac gctttccacg cacatgggtg gtgggtggg t    51
```

<210> SEQ ID NO 77
<211> LENGTH: 45
<212> TYPE: DNA
<213> ORGANISM: artificial sequence
<220> FEATURE:
<223> OTHER INFORMATION: synthetic sequence

<400> SEQUENCE: 77

```
ttgggtgggt gggtgggttt ttccacgttg ggtgggtggg tgggt          45
```

<210> SEQ ID NO 78
<211> LENGTH: 47
<212> TYPE: DNA
<213> ORGANISM: artificial sequence
<220> FEATURE:
<223> OTHER INFORMATION: synthetic sequence

<400> SEQUENCE: 78

```
ttgggtgggt gggtgggttc tttccacgct gggtgggtg ggtgggt         47
```

<210> SEQ ID NO 79
<211> LENGTH: 49
<212> TYPE: DNA

<213> ORGANISM: artificial sequence
<220> FEATURE:
<223> OTHER INFORMATION: synthetic sequence

<400> SEQUENCE: 79
ttgggtgggt gggtgggttg ctttccacgc attgggtggg tgggtgggt                49

<210> SEQ ID NO 80
<211> LENGTH: 51
<212> TYPE: DNA
<213> ORGANISM: artificial sequence
<220> FEATURE:
<223> OTHER INFORMATION: synthetic sequence

<400> SEQUENCE: 80
ttgggtgggt gggtgggttc gctttccacg cacttgggtg ggtgggtggg t              51

<210> SEQ ID NO 81
<211> LENGTH: 53
<212> TYPE: DNA
<213> ORGANISM: artificial sequence
<220> FEATURE:
<223> OTHER INFORMATION: synthetic sequence

<400> SEQUENCE: 81
ttgggtgggt gggtgggtta cgctttccac gcacattggg tgggtgggtg ggt            53

<210> SEQ ID NO 82
<211> LENGTH: 18
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (18)..(18)
<223> OTHER INFORMATION: n is T conjugated to 6-FAM

<400> SEQUENCE: 82
ttgggtgggt gggtgggn                                                   18

<210> SEQ ID NO 83
<211> LENGTH: 18
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (9)..(10)
<223> OTHER INFORMATION: nn are GT interspersed by a Tocopherol modifier
<220> FEATURE:
<221> NAME/KEY: misc_feature
<222> LOCATION: (18)..(18)
<223> OTHER INFORMATION: n is T conjugated to 6-FAM

<400> SEQUENCE: 83
ttgggtggnn gggtgggn                                                   18

<210> SEQ ID NO 84
<211> LENGTH: 18
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (9)..(10)
<223> OTHER INFORMATION: nn are GT interspersed by a Cholesterol

```
            modifier
<220> FEATURE:
<221> NAME/KEY: misc_feature
<222> LOCATION: (18)..(18)
<223> OTHER INFORMATION: n is T conjugated to 6-FAM

<400> SEQUENCE: 84
ttgggtggnn gggtgggn                                                 18

<210> SEQ ID NO 85
<211> LENGTH: 18
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is T conjugated to a Stearyl modifier
<220> FEATURE:
<221> NAME/KEY: misc_feature
<222> LOCATION: (18)..(18)
<223> OTHER INFORMATION: n is T conjugated to 6-FAM

<400> SEQUENCE: 85
ntgggtgggt gggtgggn                                                 18

<210> SEQ ID NO 86
<211> LENGTH: 16
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(16)
<223> OTHER INFORMATION: phosphorothioate backbone

<400> SEQUENCE: 86
ctatttggat gtcagc                                                   16

<210> SEQ ID NO 87
<211> LENGTH: 16
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is C conjugated to a Cholesterol modifier
<220> FEATURE:
<221> NAME/KEY: misc_feature
<222> LOCATION: (1)..(16)
<223> OTHER INFORMATION: phosphorothioate backbone

<400> SEQUENCE: 87
ntatttggat gtcagc                                                   16

<210> SEQ ID NO 88
<211> LENGTH: 16
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(1)
<223> OTHER INFORMATION: n is C conjugated to a Tocopherol modifier
<220> FEATURE:
<221> NAME/KEY: misc_feature
```

```
<222> LOCATION: (1)..(16)
<223> OTHER INFORMATION: phosphorothioate backbone

<400> SEQUENCE: 88
ntatttggat gtcagc                                                 16

<210> SEQ ID NO 89
<211> LENGTH: 34
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (9)..(10)
<223> OTHER INFORMATION: nn are GT interspersed by a Tocopherol modifier
<220> FEATURE:
<221> NAME/KEY: misc_feature
<222> LOCATION: (18)..(19)
<223> OTHER INFORMATION: nn are TC connnected by a disulfide linker
<220> FEATURE:
<221> NAME/KEY: misc_feature
<222> LOCATION: (19)..(34)
<223> OTHER INFORMATION: phosphorothioate backbone

<400> SEQUENCE: 89
ttgggtggnn gggtgggnnt atttggatgt cagc                             34

<210> SEQ ID NO 90
<211> LENGTH: 34
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (9)..(10)
<223> OTHER INFORMATION: nn are GT interspersed by a Tocopherol modifier
<220> FEATURE:
<221> NAME/KEY: misc_feature
<222> LOCATION: (18)..(19)
<223> OTHER INFORMATION: nn are TC linked by a disulfide linker
<220> FEATURE:
<221> NAME/KEY: misc_feature
<222> LOCATION: (19)..(34)
<223> OTHER INFORMATION: phosphorothioate backbone

<400> SEQUENCE: 90
ttgggtggnn gggtgggnnt atttggatgt cagc                             34

<210> SEQ ID NO 91
<211> LENGTH: 24
<212> TYPE: DNA
<213> ORGANISM: artificial sequence
<220> FEATURE:
<223> OTHER INFORMATION: primer

<400> SEQUENCE: 91
acatgccact ttggtgtttc ataa                                        24

<210> SEQ ID NO 92
<211> LENGTH: 27
<212> TYPE: DNA
<213> ORGANISM: artificial sequence
<220> FEATURE:
<223> OTHER INFORMATION: primer

<400> SEQUENCE: 92
tcttcgtaga ttgtgctgat agagaac                                     27
```

<210> SEQ ID NO 93
<211> LENGTH: 25
<212> TYPE: DNA
<213> ORGANISM: artificial sequence
<220> FEATURE:
<223> OTHER INFORMATION: primer

<400> SEQUENCE: 93
cggactatga cttagttgcg ttaca                                     25

<210> SEQ ID NO 94
<211> LENGTH: 21
<212> TYPE: DNA
<213> ORGANISM: artificial sequence
<220> FEATURE:
<223> OTHER INFORMATION: primer

<400> SEQUENCE: 94
gccatgccaa tctcatcttg t                                         21

<210> SEQ ID NO 95
<211> LENGTH: 34
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (18)..(19)
<223> OTHER INFORMATION: nn are TC connected by a disulfide linker
<220> FEATURE:
<221> NAME/KEY: misc_feature
<222> LOCATION: (19)..(36)
<223> OTHER INFORMATION: phosphorothioate backbone

<400> SEQUENCE: 95
ttgggtgggt gggtgggnnt atttggatgt cagc                           34

<210> SEQ ID NO 96
<211> LENGTH: 16
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (1)..(16)
<223> OTHER INFORMATION: phosphorothioate backbone
<220> FEATURE:
<221> NAME/KEY: misc_feature
<222> LOCATION: (16)..(16)
<223> OTHER INFORMATION: n is C conjugated to a GFWFG peptide through a
      disulfide linker

<400> SEQUENCE: 96
ctatttggat gtcagn                                               16

<210> SEQ ID NO 97
<211> LENGTH: 33
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (9)..(10)
<223> OTHER INFORMATION: nn are GG interspersed by Pep1-T (GFWFG peptide
      conjugated on dT)
<220> FEATURE:
<221> NAME/KEY: misc_feature

```
<222> LOCATION: (17)..(18)
<223> OTHER INFORMATION: nn are TC connected by a disulfide linker
<220> FEATURE:
<221> NAME/KEY: misc_feature
<222> LOCATION: (18)..(33)
<223> OTHER INFORMATION: phosphorothioate backbone

<400> SEQUENCE: 97
ttgggtggnn ggtgggnnta tttggatgtc agc                            33

<210> SEQ ID NO 98
<211> LENGTH: 32
<212> TYPE: DNA
<213> ORGANISM: artificial sequence
<220> FEATURE:
<223> OTHER INFORMATION: synthetic sequence
<220> FEATURE:
<221> NAME/KEY: misc_feature
<222> LOCATION: (5)..(6)
<223> OTHER INFORMATION: nn are GG interspersed by Pep1-T (GFWFG peptide
      conjugated on dT)
<220> FEATURE:
<221> NAME/KEY: misc_feature
<222> LOCATION: (12)..(13)
<223> OTHER INFORMATION: nn are GG interspersed by Pep1-T (GFWFG peptide
      conjugated on dT)
<220> FEATURE:
<221> NAME/KEY: misc_feature
<222> LOCATION: (16)..(17)
<223> OTHER INFORMATION: nn are TC connected by a disulfide linker
<220> FEATURE:
<221> NAME/KEY: misc_feature
<222> LOCATION: (17)..(32)
<223> OTHER INFORMATION: phosphorothioate backbone

<400> SEQUENCE: 98
ttggnnggtg gnnggnntat ttggatgtca gc                             32
```

G-QUADRUPLEX-CONTAINING ANTISENSE OLIGONUCLEOTIDES

CROSS-REFERENCE TO RELATED APPLICATION

This application makes reference to and claims the benefit of priority of the Singapore Patent Application No. 10201603451U filed on 29 Apr. 2016, the content of which is incorporated herein by reference for all purposes, including an incorporation of any element or part of the description, claims or drawings not contained herein and referred to in Rule 20.5(a) of the PCT, pursuant to Rule 4.18 of the PCT.

STATEMENT REGARDING SEQUENCE LISTING

The Sequence Listing associated with this application is provided in text format in lieu of a paper copy, and is hereby incorporated by reference into the specification. The name of the text file containing the Sequence Listing is 690148_549USPC_SEQUENCE_LISTING.txt. The text file is 23 KB was created on Aug. 19, 2020, and is being submitted electronically via EFS-Web.

FIELD OF THE INVENTION

The present invention relates to the field of oligonucleotide therapeutics, in particular to the use of antisense oligonucleotides containing G-quadruplex structures, which can be further conjugated with ligands or functional moieties for addressable delivery and enhanced properties including potency and therapeutic index.

BACKGROUND OF THE INVENTION

Antisense technology utilizes the complementary hybridization of an antisense oligonucleotide (ASO) to modulate the amount, activity, or function of the target RNA. ASO can bind to regulatory elements on a pre-mRNA or mRNA and alter the post-transcriptional control or translational profile of the target (FIG. 1A).

The sequence specificity of ASO to the target RNA renders them excellent agents for the selective knockdown of any gene for which the pathological basis is known. With the advent of genomic-based screening, genetic association studies should lead to the discovery of novel gene targets, alone or in combination, for the treatment of various pathologies. Since ASO operates at the genetic level, this further allows it to address gene targets with "undruggable" proteins, which are refractory to small molecule or antibody binding due to a lack of druggable features or inaccessible intracellular localization.

Natural oligonucleotides (DNA or RNA) have a limited half-life in the circulation due to the ubiquitous presence of native nucleases in the body. This severely limits the therapeutic potential of natural ASO compounds. To overcome this handicap, extensive chemical modifications of the nucleotide building block have been investigated. These include modifications of the phosphodiester group, sugar moiety, and nitrogenous base, or even wholesale substitution of the backbone by nucleotide analogues such as phosphorodiamidate morpholino oligos (PMO) or peptide nucleic acids (PNA).

The most widely adopted modification is the phosphorothioate (PS) backbone, which involves substitution of one of the two non-bridging phosphate (PO) oxygen atoms by a sulfur. PS modification is typically applied uniformly across ASO compounds to improve their nuclease resistance. Moreover, the PS backbone leads to enhanced serum albumin binding of ASO, thus reducing their renal clearance and consequently prolonging their circulation time.

Another common modification is the bridged nucleic acid (BNA) analogue including locked nucleic acid (LNA) and constrained ethyl (cEt). BNA is composed of a sugar that is conformationally constrained at the 2' and 4' positions through a covalent linkage, which predisposes it into an RNA-like C3'-endo puckering. LNA incorporation within ASO leads to a stronger binding affinity with the RNA target (2 to 5° C. increase in melting temperature with each LNA nucleotide substitution), hence greatly enhancing the potency of the ASO. The enhanced potency allows much lower doses of systemic ASO to be administered, thus improving the therapeutic index of the oligo. However, such modifications have a drawback of being incompatible with RNase H cleavage of the RNA target. This issue was adequately addressed by the "gapmer" design, which places these nucleotide analogues at the two flanking ends of a middle gap that is made up of DNA units. In this manner, an ASO gapmer is bestowed with improved nuclease resistance and binding affinity for the target RNA, yet still allows for RNase H cleavage of the bound RNA partner within the gap. Additionally, the "mixmer" design wherein nucleotide analogues are interspersed between DNA units, as well as fully chemically modified ASO, have also been employed to inhibit translation initiation or progression on mRNA, or to alter the splicing profile of pre-mRNA.

However, despite the progress, there still remains a considerable need in the art for innovations that overcome the limitations of existing techniques. These include the delivery of ASO to the target organ and tissue type (with minimal off-site accumulation), as well as its release into the correct cellular compartment (cytoplasm or nucleus) from endosomal vesicles.

SUMMARY OF THE INVENTION

The present invention satisfies the aforementioned need by providing novel G-quadruplex-containing conjugates.

In a first aspect, the present invention provides a conjugate comprising or consisting of (a) an antisense oligonucleotide (ASO) and (b) at least one G-quadruplex structure, wherein the ASO and the at least one G-quadruplex structure are heterologous to each other.

In various embodiments, the ASO is at least 5, preferably up to 50, most preferably between 12 to 20 nucleotides in length.

In various embodiments, the ASO is chemically modified.

In various embodiments, the ASO is modified by phosphorothioate (PS), 2'-O-methyl (2'-OMe), 2'-fluoro (2'-F), 2'-methyoxyethyl (2'-MOE), locked nucleic acid (LNA), constrained ethyl (cEt), tricyclo-DNA (tcDNA), phosphorodiamidate morpholino oligo (PMO), or peptide nucleic acid (PNA), or a combination thereof.

In various embodiments, the ASO adopts a gapmer design.

In various embodiments, the ASO adopts a mixmer design.

In various embodiments, the conjugate comprises (a) one G-quadruplex structure 5' to the ASO, (b) one G-quadruplex structure 3' to the ASO, or (c) both.

In various embodiments, wherein the at least one G-quadruplex structure comprises (a) a nucleic acid molecule comprising the nucleic acid sequence $(g)_w(n)_a(g)_x(n)_b(g)_y(n)_c(g)_z$, wherein g and n are natural or chemical analogues of guanine nucleobase and any nucleobase respectively, w, x, y, z are independently of each other integers of at least 0, a, b, c are independently of each other integers of at least 0, and the sum of integers w, x, y, z is at least 8;

(b) four nucleic acid molecules wherein each of said molecules comprises a sequence of (g), wherein z is an integer of at least 2; or (c) two nucleic acid molecules wherein each of said molecules comprises a sequence of $(g)_y(n)_b(g)_z$, wherein b is an integer of at least 0, y and z are independently of each other integers of at least 0, and the sum of integers y and z is at least 4.

In various embodiments, the nucleic acid molecule comprises the nucleic acid sequence $(g)_w(n)_a(g)_x((n)_b(g)_y(n)_c(g)_z$ wherein w, x, y, z are independently of each other integers of at least 3 and a, b, c are independently of each other integers of at least 1.

In various embodiments, the at least one G-quadruplex structure is chemically modified.

In various embodiments, the at least one G-quadruplex structure is chemically modified by phosphorothioate (PS), 2'-O-methyl (2'-OMe), 2'-fluoro (2'-F), 2'-methyoxyethyl (2'-MOE), locked nucleic acid (LNA), constrained ethyl (cEt), tricyclo-DNA (tcDNA), phosphorodiamidate morpholino oligo (PMO), or peptide nucleic acid (PNA), or a combination thereof.

In various embodiments, the loops of the at least one G-quadruplex structure comprise non-nucleosidic analogues without a base.

In various embodiments, the conjugate disclosed herein further comprises a linker connecting the at least one G-quadruplex structure to the ASO.

In various embodiments, the linker is composed of unmodified nucleotides.

In various embodiments, the linker is chemically modified.

In various embodiments, the linker is modified by phosphorothioate (PS), 2'-O-methyl (2'-OMe), 2'-fluoro (2'-F), 2'-methyoxyethyl (2'-MOE), locked nucleic acid (LNA), constrained ethyl (cEt), tricyclo-DNA (tcDNA), phosphorodiamidate morpholino oligo (PMO), or peptide nucleic acid (PNA), or a combination thereof.

In various embodiments, the linker comprises a reducible linkage (including but not limited to disulfide), an acid-labile linkage (including but not limited to acetal, ester, and hydrazone), or a protease-labile linkage (including but not limited to cathepsin and furin cleavage site).

In various embodiments, the linker is connected to a phosphate or phosphate analogue, sugar, or base on the G-tetrad core or loop of the at least one G-quadruplex structure.

In various embodiments, the linker is connected to a phosphate or phosphate analogue, sugar, or base on the ASO.

In various embodiments, the at least one G-quadruplex structure and the ASO are connected across the backbone, in the form of a contiguous nucleotide sequence.

In various embodiments, the conjugate further comprises single or multiple ligands or functional moieties conjugated to the at least one G-quadruplex structure.

In various embodiments, the ligand or functional moiety is selected from the group consisting of small molecules (including but not limited to sorafenib and vismodegib), carbohydrates (including but not limited to glucose, mannose, N-acetyl galactosamine (GalNAc), and N-acetyl glucosamine (GlcNAc)), vitamins (including but not limited to retinoid, thiamine, riboflavin, biotin, folate, cholecalciferol, and tocopherol), lipids (including but not limited to cholesterol, palmitate, stearate, and anandamide), aptamers (including but not limited to thrombin-binding aptamer), peptides, proteins, antibodies, fluorescent labels, and radiolabel tracers (including but not limited to 1,4,7,10-tetraazacyclododecane-1,4,7,10-tetraacetic acid (DOTA)).

In various embodiments, the ligand or functional moiety is connected to a phosphate or phosphate analogue, sugar, base, or non-nucleosidic analogue on the G-tetrad core or loop of the at least one G-quadruplex structure.

In various embodiments, the ASO is complementary to a portion of a DNA, pre-mRNA, mRNA, regulatory RNA, or non-coding RNA.

In a second aspect, the invention is directed to the conjugate disclosed herein for use as a medicament.

In various embodiments, the conjugate is for use in the prevention and treatment of diseases, disorders, and conditions, including but not limited to cancer or chronic symptoms.

In a third aspect, the invention encompasses a method of modulating the stability, translation, splicing, cleavage, or activity of a target nucleic acid molecule, comprising contacting the target nucleic acid molecule with a conjugate disclosed herein having an ASO complementary to a portion of the target nucleic acid molecule.

In various embodiments, the target nucleic acid molecule is a DNA, pre-mRNA, mRNA, regulatory RNA, or non-coding RNA.

In a fourth aspect, the conjugate of the present invention is employed as a selective probe for imaging or diagnostic purposes.

In a final aspect, the invention concerns use of the G-quadruplex disclosed herein in stabilizing the ASO disclosed herein.

BRIEF DESCRIPTION OF THE DRAWINGS

The invention will be better understood with reference to the detailed description when considered in conjunction with the non-limiting examples and the accompanying drawings.

FIG. 2 shows schematic diagrams of G-quadruplexes and different sites of conjugations. FIG. 2-I: (a) Chemical structure and schematic representation of a G-tetrad. B) Different folding topologies adopted by G-quadruplex (G4) forming sequences. C) Possible sites of conjugation on the G4 core and the loops. D) Non-limiting examples of ligands and biomolecules that may be attached onto a G4 scaffold for enhanced delivery of ASO. FIG. 2-II: Non-limiting examples of ligands and nucleotide analogues that have been incorporated in the A) core and B) loop of G4.

FIG. 3 shows nuclease resistance of SEA oligo. FIG. 3-I: Nuclease resistivity assay of different G4 scaffolds. A) Schematic diagram of G4s with various folding topology and sequence origin. Guanine in syn and anti configuration, and cytosine are shown in white, grey, and black, respectively. B) Denaturing PAGE images of G4s (2 pmol) following incubation in human serum type AB for various time intervals; FIG. 3-II: comparative denaturing PAGE images of A) conventional antisense oligonucleotides (ASO) versus B) structure-enhanced antisense oligo (SEA oligo) following incubation in human serum type AB for various time intervals. Constructs with phosphate backbone and phosphorothioate backbone are indicated with subscript O and S respectively.

FIG. 4 shows compatibility of SEA oligos with RNase H enzyme degradation of target RNA. FIG. 4-I: RNase H assay of conventional ASO versus SEA oligo. A) Schematic representation of RNase H mode of action. B) Denaturing PAGE image of RNase H treated ASO and SEA oligo. FIG. 4-II: denaturing PAGE images demonstrating RNase H compatibility of SEA oligo with single G4 attachment (middle and right) in comparison with conventional ASO (left). ASO and SEA oligo were each hybridized with 2 pmol 5' FAM-labelled RNA to form RNA/DNA heteroduplex with A) 5' RNA overhang; B) 3' RNA overhang, and treated with RNase H at 37° C. for 1 hour. FIG. 4-III: denaturing PAGE images demonstrating RNase H compatibility of SEA oligo (right) with double G4 attachments in comparison with conventional ASO (left). ASO and SEA oligo were each hybridized with 2 pmol 5' FAM-labelled RNA to form RNA/DNA heteroduplex with 5' and 3' RNA overhang, and treated with RNase H at 37° C. for 1 hour.

FIG. 7 shows the various combinations that single and multiple ligands can be conjugated onto a G4 structure. FIG. 7-I: Single or multiple ligands can be conjugated onto the G-tetrad core or loops in multiple combinations. FIG. 7-II: 1D imino (left) and aromatic (right) proton NMR spectra of (A) T95-2T, (B) T95-2T(GalNAc-15), (C) T95-2T(GalNAc-17), (D) T95-2T(GalNAc-16,17), and (E) T95-2T(GalNAc-15,16,17). Peaks corresponding to the N-acetyl amide proton of GalNAc are labeled with asterisks. Schematic illustrating the number of conjugated GalNAc units are shown on the right.

DETAILED DESCRIPTION OF THE INVENTION

The following detailed description refers to, by way of illustration, specific details and embodiments in which the invention may be practiced. These embodiments are described in sufficient detail to enable those skilled in the art to practice the invention. Other embodiments may be utilized and structural, and logical changes may be made without departing from the scope of the invention. The various embodiments are not necessarily mutually exclusive, as some embodiments can be combined with one or more other embodiments to form new embodiments.

Unless otherwise defined, all technical and scientific terms used herein have the same meaning as commonly understood by one of ordinary skill in the art. In case of conflict, the present document, including definitions, will control.

The objective of the present invention is to provide improved antisense technologies.

Figure 1:
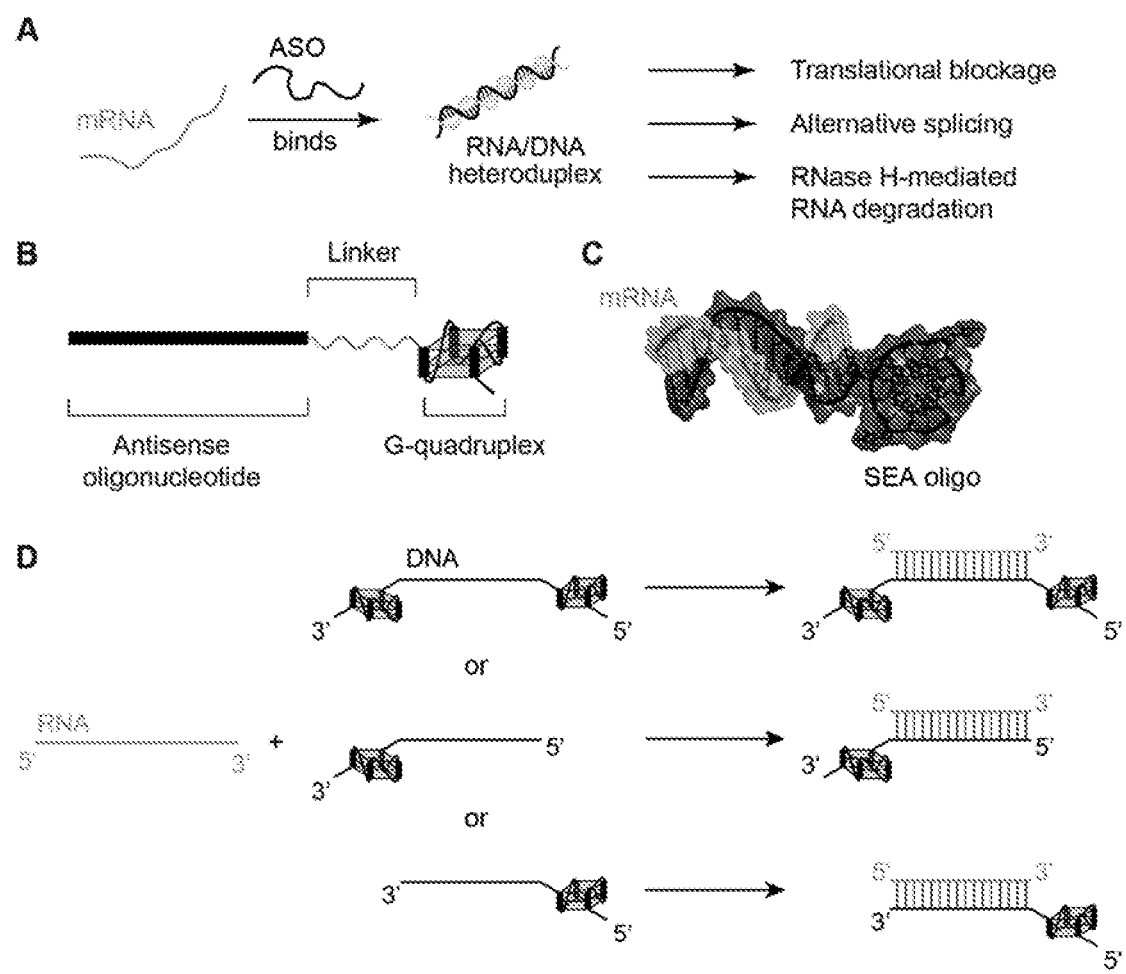
FIG. 1 shows: (a) ASO binding to RNA target based on complementary hybridization, leading to translational blockage, alternative splicing, or RNase H degradation of the RNA. (b) Schematic diagram of a structure-enhanced antisense oligo (SEA oligo), with the ASO connected to a G-quadruplex structure through a linker. (c) Structural model showing the hybridization of SEA oligo with a target RNA. (d) Schematic diagram showing the various constructs of SEA oligo and their binding of the RNA target.

To this end, in a first aspect, the present invention provides a conjugate comprising, consisting essentially of, or consisting of (a) an antisense oligonucleotide (ASO) and (b) at least one G-quadruplex (G4) structure, wherein the ASO and the at least one G-quadruplex structure are heterologous to each other (FIGS. 1B & 1C are exemplary and non-limiting schematic diagrams illustrating such conjugates). The conjugate is henceforth denoted as structure-enhanced antisense oligo (SEA oligo).

The term "antisense oligonucleotide" or "ASO" is used broadly herein and encompasses a single-stranded oligomer comprising ribonucleotides, deoxyribonucleotides, modified ribonucleotides, modified deoxyribonucleotides or a combination thereof that is complementary to a portion of a target nucleic acid molecule. The target nucleic acid molecule of the ASO of the present invention may be a DNA, pre-mRNA, mRNA, regulatory RNA, or non-coding RNA.

Without wishing to be bound to any theory, the ASO binds to the target nucleic acid molecule through sequence-specific complementary hybridization and modulates the stability, translation, splicing, cleavage, or activity thereof. Those skilled in the art will recognize that the exact length of the ASO and its degree of complementarity with its target nucleic acid molecule will depend upon the specific target selected, including but not limited to the sequence and base composition of the target.

The ASO of the present invention is at least 5, preferably up to 50 nucleotides in length, for example, 5 to 50 nucleotides in length, 8 to 40 nucleotides in length, 12 to 30 nucleotides in length, or 20 to 25 nucleotides in length. In preferred embodiments, the ASO is at least 12, preferably up to 30 nucleotides in length. In some embodiments, the ASO is about 12, 13, 14, 15, 16, 17, 18, 19, 20, 21, 22, 23, 24, 25, 26, 27, 28, 29, or 30 nucleotides in length. In the most preferred embodiments, the ASO is between 12 to 20 nucleotides in length.

The ASO of the invention is constructed and arranged such as to bind selectively with the target nucleic acid molecule under physiological conditions, i.e., to hybridize substantially more to the target sequence than to any other sequence in the target cell under physiological conditions. The term "physiological conditions" is to be understood as referring to the physicochemical conditions (temperature, pH, ionic strength, viscosity, and the like) present intracellularly or extracellularly.

The term "complementary" is used herein to describe a first nucleotide sequence in relation to a second nucleotide sequence and refers to the ability of an oligonucleotide or polynucleotide comprising the first nucleotide sequence to hybridize to and form a duplex structure under physiological conditions with an oligonucleotide or polynucleotide comprising the second nucleotide sequence. Such hybridization is ordinarily the result of base-specific hydrogen bonding between complementary strands, preferably to form Watson-Crick or Hoogsteen base pairs, although other modes of hydrogen bonding, as well as base stacking can also lead to hybridization are also encompassed herein. However, in particular embodiments, "complementary" means hybridization of Watson-Crick base pairing only. "Complementary" sequences, as used herein, may also include or be formed entirely from base pairs formed from non-natural and modified nucleotides, insofar the above requirements with respect to their ability to hybridize are fulfilled.

The ASO of the invention does not necessarily have to be fully complementary to the target nucleic acid molecule and some mismatches therebetween may be tolerated, given that the ASO is at least partially or substantially complementary to the target nucleic acid molecule to hybridize thereto and form a stable hybrid under physiological conditions. For instance, in some embodiments, the ASO is at least 75%, 80%, 85%, 90%, 95%, 96%, 97%, 98%, or 99%, or preferably 100% complementary to the target nucleic acid molecule, as calculated based on the length of the ASO. Complementarity can be determined by means known in the art, in particular alignment tools such as BLAST programs (basic local alignment search tools) and PowerBLAST programs.

The ASO of the present invention may be modified in part or in full, for example, by chemical analogues including but not limited to phosphorothioate (PS), 2'-O-methyl (2'-OMe), 2'-fluoro (2'-F), 2'-methyoxyethyl (2'-MOE), locked nucleic acid (LNA), constrained ethyl (cEt), tricyclo-DNA (tcDNA), phosphorodiamidate morpholino oligo (PMO), or peptide nucleic acid (PNA), or a combination thereof. In certain embodiments, the ASO adopts a gapmer design. In certain embodiments, the ASO adopts a mixmer design. In certain embodiments, the ASO is fully chemically modified. These chemical modifications may improve nuclease resistance of the ASO or binding affinity of the ASO for its intended RNA target. The design of an ASO adopting a "gapmer" design or a "mixmer" design is within the purview of one of skill in the art.

The term "G-quadruplex" as used herein refers to a four-stranded helical nucleic acid structure comprising multiple stacked G-tetrads (FIG. 2-IA), each of which consists of four guanine bases or chemical analogues of guanine that associate in a cyclical manner through Hoogsteen hydrogen bonds and may be further stabilized through coordination to a cation in the center. The body of stacked G-tetrads, comprising a total of 2 or more layers, is collectively referred to as the G-tetrad core. Each of the four guanine columns constituting the G-tetrad core can arise from a single (continuous column) or two (discontinuous column) separate guanine stretch/es. The G-quadruplex structure of the present invention is thus a robust four-stranded helical structure spontaneously formed by G-rich oligonucleotide sequences under physiological conditions. Said G-quadruplex structure has two major structural components, a four-stranded G-tetrad core and three intervening loops (FIG. 2I-C).

G-quadruplex structures are highly diverse with regards to their relative strand orientations and loop types (FIG. 2I-B), resulting in different topologies including (a) parallel-type in which four strands point in the same direction; (b) hybrid "3+1" type in which three strands point in one direction and the fourth strand points in the opposite one; (iii) antiparallel-type in which two strands point in one direction and two strands point in the opposite direction. These topologies lead to different structural molecular shapes, with various loops and grooves of different size and accessibility (Phan A. T., *FEBS J.* 2010, 277, 1107). The structural polymorphism of G-quadruplexes depends on their nucleotide sequences and the environmental conditions.

In various embodiments, the G-quadruplex structure comprises (a) a nucleic acid molecule comprising the nucleic acid sequence $(g)_w(n)_a(g)_x((n)_b(g)_y(n)_c(g)_z$, wherein w, x, y, z are independently of each other integers of at least 0, a,b,c are independently of each other integers of at least 0, and the sum of integers w, x, y, z is at least 8; (b) four nucleic acid molecules, wherein each of said molecules comprises a sequence of $(g)_z$, wherein z is an integer of at least 2; or (c) two nucleic acid molecules, wherein each of said molecules comprises a sequence of $(g)_y(n)_b(g)_z$ wherein b is an integer of at least 0, y and z are independently of each other integers of at least 0, and the sum of integers y and z is at least 4. In various embodiments, the nucleic acid molecule comprises the nucleic acid sequence $(g)_w(n)_a(g)_x((n)_b(g)_y(n)_c(g)_z$, wherein w, x, y, z are independently of each other integers of at least 3 and a, b, c are independently of each other integers of at least 1. The term "g", as used herein, relates to a guanine nucleobase or its chemical analogues. The term "n", as used herein, relates to a nucleotide having a base that is selected from the group consisting of adenine, guanine, cytosine, uracil, and thymine, or their chemical analogues.

The G-tetrad core and loops of the G-quadruplex structure may be chemically modified in part or in full, for example, with chemical analogues including but not limited to, PS, 2'-OMe, 2'-F, 2'-MOE, LNA, cEt, tcDNA, PMO, and PNA, or a combination thereof. In certain embodiments, the loops may comprise non-nucleosidic analogues without a base. There is a diverse range of G-quadruplex topologies arising from the combinatorial arrangement of the core and loops (FIG. 2I-B).

In accordance with the present invention, the ASO and the at least one G-quadruplex structure are heterologous to each other, meaning that they are not found together in a cell in nature.

The conjugate of the present invention comprises at least one G-quadruplex structure under physiological conditions. The term "at least one", as used herein particularly in relation to the G-quadruplex structure, relates to one or more, in particular 1, 2, 3, 4, 5, 6, 7, 8, 9, 10 or more. In preferred embodiments, the conjugate comprises up to 4, preferably up to 3, more preferably 1 or 2 G-quadruplex structure/s. In the most preferred embodiments, the conjugate comprises (a) one G-quadruplex structure 5' to the ASO, (b) one G-quadruplex structure 3' to the ASO, or (c) both (FIG. 1D).

In various embodiments, the conjugate further comprises a linker connecting the at least one G-quadruplex structure to the ASO (FIG. 1B).

The linker may be cleavable or non-cleavable in nature. In certain embodiments, the linker may be a nucleotide or nucleotide analogue, and may be unmodified, chemically modified in part or in full, for example, with chemical analogues including but not limited to, PS, 2'-OMe, 2'-F, 2'-MOE, LNA, cEt, tcDNA, PMO, and PNA, or a combination thereof. In certain embodiments, the linker may comprise a reducible linkage (including but not limited to disulfide), an acid-labile linkage (including but not limited to acetal, ester, and hydrazone), or a protease-labile linkage (including but not limited to cathepsin and furin cleavage site). The attachment point of the linker on the G-quadruplex structure can be any part of the G-tetrad core or loop. In certain embodiments, the linker is connected to a phosphate or phosphate analogue on the G-tetrad core or loop. In certain embodiments, the linker is connected to the sugar on the G-tetrad core or loop. In certain embodiments, the linker is connected to the base on the G-tetrad core or loop. The attachment point of the linker on the ASO can be any part of the ASO, preferably on either one flanking end or both flanking ends of the ASO. In certain embodiments, the linker is connected to a phosphate or phosphate analogue on the ASO. In certain embodiments, the linker is connected to the sugar on the ASO. In certain embodiments, the linker is connected to the base on the ASO. In the preferred embodiments, the G-quadruplex structure and the ASO are connected across the backbone, in the form of a contiguous nucleotide sequence, which is compatible with the automated synthesis of oligonucleotides.

Targeted delivery of ASO to its desired site of action remains one of the major challenges of the field. This entails delivery of ASO to the target organ and tissue type (with minimal off-site accumulation), as well as its release into the correct cellular compartment (cytoplasm or nucleus) from endosomal vesicles, otherwise known as the functional uptake of the oligonucleotide. Various approaches have been employed to accomplish this goal, including the packaging of ASO within delivery vehicles (e.g. liposomal particles or cationic polymers). However, toxicity and off-target issues still hamper their widespread utility.

Another approach involves the use of ligand conjugates of ASO, which will be directed towards organs or tissues showing an overexpression of the native receptors for the ligands. Recent advances include the conjugation of multiple N-acetyl galactosamine (GalNAc) units onto ASO, which tremendously enhances their delivery to liver hepatocytes with an abundance of the cognate asialoglycoprotein receptors (ASGPR). Since internal modifications within ASO could interfere with target hybridization, ligand conjugation sites are largely restricted to the two flanking ends. In certain cases, single-ligand conjugates were shown to be insufficient to induce efficient uptake, necessitating the design of a sophisticated scaffold for the presentation of multiple ligands for receptor recognition. This complicates and limits the scalability between different receptor-ligand pairs. Nevertheless, following the same principle, myriad other ligands can be conjugated onto ASO to assist in their targeted delivery. These can range in size from simple ligands such as small molecules, carbohydrates, vitamins, lipids, and peptides, up to macromolecules including aptamers, proteins, and even antibodies (FIG. 2-ID).

In this context, the G-quadruplex structure of the conjugate of the invention may be further conjugated with single or multiple ligands or functional moieties in a controllable and modular fashion, leading to desirable traits including addressable delivery, enhanced potency, or additional functionality of the ASO. By the term "ligand" or "functional moiety", as used herein, any chemical molecule or group is meant that can be attached to the G-quadruplex structure, including but not limited to small molecules, carbohydrates, vitamins, lipids, peptides, aptamers, proteins, antibodies, and detectable tags.

The ligands or functional moieties may be pre-conjugated onto phosphoramidites, which are the monomeric building blocks for the automated synthesis of oligonucleotides, and incorporated onto the oligonucleotide chain during automated synthesis, or they may be incorporated onto the G-quadruplex structure post-synthetically using complementary conjugation chemistry. The conjugation site may be any position on the nucleotide building block of the G-tetrad core (FIG. 2-IIA) and loop (FIG. 2-IIB). In certain embodiments, the ligand is conjugated onto the phosphate or phosphate analogue on the G-tetrad core or loop. In certain embodiments, the ligand is connected to the sugar on the G-tetrad core or loop. In certain embodiments, the ligand is connected to the base on the G-tetrad core of loop. In certain embodiments, the ligand is connected to a non-nucleosidic analogue. The ligands that may be conjugated include, but are not limited to, small molecules (including but not limited to sorafenib and vismodegib), carbohydrates (including but not limited to glucose, mannose, GalNAc, and GlcNAc), vitamins (including but not limited to retinoid, thiamine, riboflavin, biotin, folate, cholecalciferol, and tocopherol), lipids (including but not limited to cholesterol, palmitate, stearate, and anandamide), aptamers (including but not limited to thrombin-binding aptamer), peptides, proteins, antibodies, fluorescent labels, and radiolabel tracers (including but not limited to DOTA).

Without wishing to be bound to any particular theory, the presence of a G-quadruplex structure at either one end (5' or 3') or both ends (5' and 3') of the ASO is compatible with RNase H degradation of the bound RNA target of the ASO (FIG. 4). The conjugate of the present invention exhibits numerous advantages over traditional ASO design, including but not limited to increased nuclease resistance (FIG. 3) and enhanced gene knockdown activity of the ASO relative to the standard ASO.

In addition, the presence of a G-quadruplex structure in the conjugate described herein creates a hub for oligonucleotide modification which does not interfere with the hybridization of the ASO/target complex. Unlike the standard ASO which can only accommodate up to two bulky moieties, one on each terminus of the ASO, the conjugate of the present invention can potentially accommodate as many attachments as the participating nucleotides within the G-quadruplex without structural distortion to the resulting ASO/target complex. Modification of a G-quadruplex structure within the conjugate therefore provides a method for overcoming the numerous barriers to delivery currently impeding progression of antisense therapeutic development in the industry.

In a second aspect, the invention is directed to the conjugate disclosed herein for use as a medicament.

The conjugate of the present invention may be used as a medicament, preferably for the prevention or treatment of diseases, disorders, and conditions. The terms "disease", "disorder", or "condition" are used interchangeably herein, and refer to any alteration in state of the body or of some of the organs, interrupting or disturbing the performance of the functions or causing symptoms such as discomfort, dysfunction, distress, or even death to the person afflicted or those in contact with a person, in particular to cancer or chronic symptoms.

Cancers treatable by the conjugate of the invention include, but are not limited to, breast cancer, lung cancer, head and neck cancer, brain cancer, abdominal cancer, colon cancer, colorectal cancer, esophageal cancer, parapharyngeal cancer, gastrointestinal cancer, glioma, liver cancer, hepatocellular cancer, parotid gland cancer, tongue cancer, neuroblastoma, osteosarcoma, ovarian cancer, renal cancer, pancreatic cancer, retinoblastoma, cervical cancer, uterine cancer, Wilm's tumor, multiple myeloma, skin cancer, lymphoma, leukemia, blood cancer, anaplastic thyroid tumor, sarcoma of the skin, melanoma, adenocystic tumor, hepatoid tumor, non-small cell lung cancer, chondrosarcoma, pancreatic islet cell tumor, prostate cancer, ovarian cancer, gall bladder cancer, urinary bladder cancer, renal cancer, urinary tract cancer, vulvar cancer, vaginal cancer, anal cancer, penile cancer, or carcinomas including but not limited to squamous cell carcinoma of the head and neck, colorectal carcinoma, glioblastoma, cervical carcinoma, endometrial carcinoma, gastric carcinoma, pancreatic carcinoma, leiomyosarcoma and breast carcinoma. In some embodiments, cancers treatable by the conjugates provided herein are hematological cancers, including but not limited to multiple myeloma, acute myelogenous leukemia, acute/chronic lymphoblastic leukemia, hairy-cell leukemia, follicular lymphoma, plasmacytoma, diffuse large B-cell lymphoma, Hodgkin's lymphoma, Non-Hodgkin's lymphoma and the like. In some embodiments, cancers treated by the conjugates provided herein are carcinomas. In some embodiments, cancers treated by the conjugates provided herein are hematological cancers. In some embodiments, cancers treated by the conjugates provided herein are sarcomas. In some embodiments, cancers treated by the conjugates provided herein are solid tumors.

Chronic symptoms treatable by the conjugate of the invention include, but are not limited to, to the following list of diseases; acquired immune deficiency syndrome (AIDS), attention deficit/hyperactivity disorder (ADHD), allergies, amyotrophic lateral sclerosis (ALS), Alzheimer's disease, arthritis, asthma, behcet's syndrome, bipolar disorder, bronchitis, cancer, cardiomegaly, cardiomyopathy, Crohn's disease, chronic cough, chronic fatigue syndrome (CFS), chronic obstructive pulmonary disease (COPD), congestive heart failure, cystic fibrosis, depression, diabetes, drug addiction, alcohol addiction, emphysema, fibromyalgia, gastroesophageal reflux disease (GERD), gout, hansen's disease, hunter syndrome, Huntington's disease, hyperlipidemia, hypertension, Marfan syndrome, mesenteric lymphadenitis, multiple sclerosis, migraines, myelofibrosis, nephrotic syndrome, obesity, Parkinson's disease, pneumoconiosis (interstitial lung diseases), pulmonary edema, pulmonary fibrosis, pulmonary hypertension, reactive airway disease, sarcoidosis, scleroderma, systemic lupus erythematosus, and ulcerative colitis.

As long as the genetic cause of a disease, disorder, or condition is known, a conjugate specific for the RNA of the causal genes may be developed in accordance with the present invention. Off-target effects of such conjugates may be minimized by optimizing the sequence design of the ASO.

Prior to its use as a medicament or in the treatment of a disease, disorder, or condition, the conjugate of the invention may need to be formulated into a pharmaceutical composition further comprising a pharmaceutically acceptable carrier. The skilled artisan would also realize that proper formulation is dependent upon the route of administration selected for the specific application, and the proper route and mode of administering the conjugate of the invention to a subject should be determined on a case-by-case basis. Suitable pharmaceutical compositions and dosage forms may be prepared using conventional methods known to those in the field of pharmaceutical formulation and described in the pertinent texts and literature, e.g., in *Remington: The Science and Practice of Pharmacy.*

In a third aspect, the invention encompasses a method of modulating the stability, translation, splicing, cleavage, or activity of a target nucleic acid molecule, comprising contacting the target nucleic acid molecule with a conjugate of the invention having an ASO complementary to a portion of the target nucleic acid molecule.

In various embodiments, the target nucleic acid molecule is a DNA, pre-mRNA, mRNA, regulatory RNA, or noncoding RNA.

The term "modulate" as used herein is meant to refer to any changes in biological state, i.e. increasing, decreasing, and the like.

It should be noted that, counterintuitively, ASO may also upregulate translation of a target RNA. For example, it has been shown that ASO binding to upstream ORF (uORF) of a mRNA leads to increased protein translation. In addition, ASO binding to the ends of mRNA can slow down native mRNA degradation (U.S. Pat. No. 2015/0050738 A1), thereby leading to higher protein production. Therefore, without wishing to be bound to any theory, the conjugate of the invention may be used to modulate the stability, translation, splicing, cleavage, or activity of its target nucleic acid molecule, either positively or negatively.

In a fourth aspect, the conjugate of the present invention is employed as a selective probe for imaging or diagnostic purposes.

In a final aspect, the invention concerns use of the G-quadruplex disclosed herein in stabilizing the ASO disclosed herein.

The present invention is further illustrated by the following examples. However, it should be understood, that the invention is not limited to the exemplified embodiments.

EXAMPLES

Example 1: Nuclease Resistance of SEA Oligo

Nuclease digestion assay. Oligonucleotides labelled with 6-FAM on 5' or 3' end were dissolved in buffer containing 20 mM potassium phosphate (KPi), 70 mM KCl, pH 7.0 to 20 µM concentration, heated to 95° C. and cooled slowly to room temperature. Aliquots of human serum type AB were mixed with FAM-labelled oligonucleotides (final concentration 2 µM) and incubated at 37° C. for time points of 0, 0.5, 1, 3, 24, 48, 120 h. At each time interval, 2 µL aliquots were added to stop buffer containing 95% formamide, 50 mM EDTA, 0.025% SDS, chilled on ice for 15 min and subsequently heat-denatured at 95° C. for 1 h. The denatured oligonucleotide samples were resolved by denaturing polyacrylamide gel electrophoresis on gels containing 20% acrylamide, 7 M urea, 1× Tris-Borate-EDTA, and visualized through fluorescence gel imaging.

Due to its robust nature, said G-quadruplex structure affords the ASO further nuclease resistance (FIG. 3), beyond that which is provided through chemical modifications of the ASO.

TABLE 1-1

Table of constructs used in the nuclease digestion assay.

| Name | Construct type*a* | SEQ ID NO: | Sequence (5' to 3'; X = DNA; * = phosphorothioate bond; *F* = 6-FAM) |
|---|---|---|---|
| So | ssDNA PO | 1 | AACACGTCTATACGC *F* |
| Ss | ssDNA PS | 2 | A*A*C*A*C*G*T*C*T*A*T*A*C*G*C *F* |
| G4 | 3-layer | 3 | TTGGGTGGGTGGGTGGGT *F* |

TABLE 1-1-continued

Table of constructs used in the nuclease digestion assay.

| Name | Construct type[a] | SEQ ID NO: | Sequence (5' to 3'; X = DNA; * = phosphorothioate bond; F = 6-FAM) |
|---|---|---|---|
| | parallel G4 PO | | |
| G41 | 3-layer c-myc parallel G4 PO | 4 | F TGAGGGTGGTGAGGGTGGGGAAGG |
| G42 | 6-layer interlocked dimer G4 PO | 5 | GGGGTGGGAGGAGGGT F |
| HT1 | 3-layer HT (3 + 1) form 1 G4 PO | 6 | F TTGGGTTAGGGTTAGGGTTAGGGA |
| HT2 | 2-layer HT basket type G4 PO | 7 | GGGTTAGGGTTAGGGTTAGGGT F |
| HT3 | 3-layer HT chair-type G4 PO | 8 | F AGGGCTAGGGCTAGGGCTAGGG |
| ZG4 | 4-layer left-handed G4 PO | 9 | TGGTGGTGGTGGTTGTGGTGGTGGTGTT F |
| G4o-So | G4 PO + ssDNA PO | 10 | TTGGGTGGGTGGGTGGGTAACACGTCTATACGC F |
| G4s-Ss | G4 PS + ssDNA PS | 11 | T*T*G*G*G*T*G*G*G*T*G*G*G*T*G*G*G*T*A*A*C*A*C*G*T*C*T*A*T*A*C*G*C F |
| G4o-So-G4o | G4 PO + ssDNA PO + G4 PO | 12 | TTGGGTGGGTGGGTGGGTAACACGTCTATACGCTGGGTGGGTGGGTGGGT F |
| G4s-Ss-G4s | G4 PS + ssDNA PS + G4 PS | 13 | T*T*G*G*G*T*G*G*G*T*G*G*G*T*G*G*G*T*A*A*C*A*C*G*T*C*T*A*T*A*C*G*C*T*G*G*G*T*G*G*G*T*G*G*G*T*G*G*G*T F |

[a] ssDNA = single-stranded DNA; G4 = G-quadruplex; HT = human telomeric; PO = phosphate backbone; PS = phosphorothioate backbone

Example 2: Compatibility of SEA Oligo with RNase H Degradation of RNA Target Preparation of RNA/DNA heteroduplex substrates. 200 nM of 5' FAM-labelled RNA was incubated with 3-fold excess of DNA in buffer containing 20 mM Tris-HCl (pH 7.5), 20 mM KCl. The reaction was heated to 90° C. for 5 min and cooled slowly to 37° C. RNase inhibitor (0.6 U/4) and 1 mM MgCl$_2$ were subsequently added, and the reaction was incubated at 37° C. for 16 h.

RNase H assay of RNA/DNA heteroduplex substrates. E. coli RNase H enzymes were pre-incubated in buffer containing 20 mM Tris-HCl (pH 7.5), 20 mM KCl, 1 mM MgCl$_2$, 1 mM tris(2-carboxyethyl)phosphine hydrochloride at 37° C. for 5 min. 1 μL of heteroduplex substrate (final concentration of 100 nM) was digested with 0.5 U of RNase H at 37° C. for 1 h, and the reaction was terminated by the addition of 2× volume of stop buffer (95% formamide, 18 mM EDTA, 0.025% SDS) and heat-denatured at 95° C. for 5 min. The digested substrates were resolved in 20% denaturing polyacrylamide gel and visualized via fluorescence imaging.

The presence of said G-quadruplex structure at either one end (5' or 3') or both ends (5' and 3') of the ASO (FIG. 1D) is compatible with RNase H-mediated degradation of the bound RNA target of the ASO (FIG. 4).

TABLE 2-1

List of oligonucleotides utilized in RNA/DNA heteroduplex formation.

| Name | SEQ ID NO: | Sequence (X = DNA, Y = RNA, F = 6-FAM; \| = base-pairing) |
|---|---|---|
| F-rA-20 | 14 | F ACUGUGCGUGGAAAGCGUAG |
| dA6 | 15 | CTACGC |

TABLE 2-1-continued

List of oligonucleotides utilized in RNA/DNA heteroduplex formation.

| Name | SEQ ID NO: | Sequence (X = DNA, Y = RNA, F = 6-FAM; \| = base-pairing) |
|---|---|---|
| dA8 | 16 | CTACGCTT |
| dA10 | 17 | CTACCGTTTC |
| dA12 | 18 | CTACGCTTTCCA |
| dA14 | 19 | CTACGCTTTCCACG |
| dA16 | 20 | CTACGCTTTCCACGCA |
| dA18 | 21 | CTACGCTTTCCACGCACA |
| dA20# | 22 | CTACGCTTTCCACGCAGAGT |
| d6A | 23 | CACAGT |
| d8A | 24 | CGCACAGT |
| d10A | 25 | CACGCACACT |
| d12A | 26 | TCCACGCACAGT |
| d14A | 27 | TTTCCACGCACAGT |
| d16A | 28 | GCTTTCCACGCACAGT |
| d18A | 29 | ACGCTTTCCACGCACAGT |
| d20A# | 30 | CTACGCTTTCCACGCACAGT |
| dA8i | 31 | TTTCCACG |
| dA10i | 32 | CTTTCCACGC |
| dA12i | 33 | GCTTTCCACGCA |
| dA14i | 34 | CGCTTTCCACGCAC |
| dA16i | 35 | ACGCTTTCCACGCACA |
| dA6-G4 | 36 | TTGGGTGGGTGGGTGGGTTCTACGC |
| dA8-G4 | 37 | TTGGGTGGGTGGGTGGGTTCTACGCTT |
| dA10-G4 | 38 | TTGGGTGGGTGGGTGGGTTCTACGCTTTC |
| dA12-G4 | 39 | TTGGGTGGGTGGGTGGGTTCTACGCTTTCCA |
| dA14-G4 | 40 | TTGGGTGGGTGGGTGGGTTCTACGCTTTCCACG |
| dA16-G4 | 41 | TTGGGTGGGTGGGTGGGTTCTACGCTTTCCACGCA |
| dA18-G4 | 42 | TTGGGTGGGTGGGTGGGTTCTACGCTTTCCACGCACA |
| dA20-G4& | 43 | TTGGGTGGGTGGGTGGGTTCTACGCTTTCCACGCACAGT |
| dG4-6A | 44 | CACAGTTTGGGTGGGTGGGTGGGTT |
| dG4-8A | 45 | CGCACAGTTTGGGTGGGTGGGTGGGTT |
| dG4-10A | 46 | CACGCACAGTTTGGGTGGGTGGGTGGGTT |
| dG4-12A | 47 | TCCACGCACAGTTTGGGTGGGTGGGTGGGTT |

TABLE 2-1-continued

List of oligonucleotides utilized in RNA/DNA heteroduplex formation.

| Name | SEQ ID NO: | Sequence (X = DNA, Y = RNA, F = 6-FAM; \| = base-pairing) |
|---|---|---|
| dG4-14A | 48 | TTTCCACGCACAGTTTGGGTGGGTGGGTGGGTT |
| dG4-16A | 49 | GCTTTCCACGCACAGTTTGGGTGGGTGGGTGGGTT |
| dG4-18A | 50 | ACGCTTTCCACGCACAGTTTGGGTGGGTGGGTGGGTT |
| dG4-20A$^S$ | 51 | CTACGCTTTCCACGCACAGTTTGGGTGGGTGGGTGGGTT |
| dG4-A6 | 52 | CTACGCTTGGGTGGGTGGGTGGGTT |
| dG4-A10 | 53 | CTACGCTTTCTTGGGTGGGTGGGTGGGTT |
| dG4-A14 | 54 | CTACGCTTTCCACGTTGGGTGGGTGGGTGGGTT |
| dG4-A18 | 55 | CTACGCTTTCCACGCACATTGGGTGGGTGGGTGGGTT |
| dG4-A20$^S$ | 56 | CTACGCTTTCCACGCACAGTTTGGGTGGGTGGGTGGGTT |
| d6A-G4 | 57 | TTGGGTGGGTGGGTGGGTTCACAGT |
| d10A-G4 | 58 | TTGGGTGGGTGGGTGGGTTCACGCACAGT |
| d14A-G4 | 59 | TTGGGTGGGTGGGTGGGTTTTCCACGCACAGT |
| d18A-G4 | 60 | TTGGGTGGGTGGGTGGGTTACGCTTTCCACGCACAGT |
| d20A-G4$^\&$ | 61 | TTGGGTGGGTGGGTGGGTTCTACGCTTTCCACGCACAGT |
| dG4T-A8i-TTG4 | 62 | TTGGGTGGGTGGGTGGGTTTTCCACGTTGGGTGGGTGGGTGGGT |
| dG4T-A10i-TTG4 | 63 | TTGGGTGGGTGGGTGGGTCTTTCCACGCTTGGGTGGGTGGGTGGGT |
| dG4T-A12i-TTG4 | 64 | TTGGGTGGGTGGGTGGGTGCTTTCCACGCATTGGGTGGGTGGGTGGGT |
| dG4T-A14i-TTG4 | 65 | TTGGGTGGGTGGGTGGGTCGCTTTCCACGCACTTGGGTGGGTGGGTGGGT |
| dG4T-A16i-TTG4 | 66 | TTGGGTGGGTGGGTGGGTACGCTTTCCACGCACATTGGGTGGGTGGGTGGGT |
| dG4-A8i-G4 | 67 | TTGGGTGGGTGGGTGGGTTTCCACGGGGTGGGTGGGTGGGT |
| dG4-A10i-G4 | 68 | TTGGGTGGGTGGGTGGGCTTTCCACGCGGGTGGGTGGGTGGGT |
| dG4-A12i-G4 | 69 | TTGGGTGGGTGGGTGGGGCTTTCCACGCAGGGTGGGTGGGTGGGT |

TABLE 2-1-continued

List of oligonucleotides utilized in RNA/DNA heteroduplex formation.

| Name | SEQ ID NO: | Sequence (X = DNA, Y = RNA, *F* = 6-FAM; \| = base-pairing) |
|---|---|---|
| dG4-A14i-G4 | 70 | TTGGGTGGGTGGGTGGGCGCTTTCCACGCACGGGTGGGTGGGTGGGT |
| dG4-A16i-G4 | 71 | TTGGGTGGGTGGGTGGGACGCTTTCCACGCACAGGGTGGGTGGGTGGGT |
| dG4T-A8i-TG4 | 72 | TTGGGTGGGTGGGTGGGTTTTCCACGTGGGTGGGTGGGTGGGT |
| dG4T-A10i-TG4 | 73 | TTGGGTGGGTGGGTGGGTCTTTCCACGCTGGGTGGGTGGGTGGGT |
| dG4T-A12i-TG4 | 74 | TTGGGTGGGTGGGTGGGTGCTTTCCACGCATGGGTGGGTGGGTGGGT |
| dG4T-A14i-TG4 | 75 | TTGGGTGGGTGGGTGGGTCGCTTTCCACGCACTGGGTGGGTGGGTGGGT |
| dG4T-A16i-TG4 | 76 | TTGGGTGGGTGGGTGGGTACGCTTTCCACGCACATGGGTGGGTGGGTGGGT |
| dG4TT-A8i-TTG4 | 77 | TTGGGTGGGTGGGTGGGTTTTTCCACGTTGGGTGGGTGGGTGGGT |
| dG4TT-A10i-TTG4 | 78 | TTGGGTGGGTGGGTGGGTTCTTTCCACGCTTGGGTGGGTGGGTGGGT |
| dG4TT-A12i-TTG4 | 79 | TTGGGTGGGTGGGTGGGTTGCTTTCCACGCATTGGGTGGGTGGGTGGGT |
| dG4TT-A14i-TTG4 | 80 | TTGGGTGGGTGGGTGGGTTCGCTTTCCACGCACTTGGGTGGGTGGGTGGGT |
| dG4TT-A16i-TTG4 | 81 | TTGGGTGGGTGGGTGGGTTACGCTTTCCACGCACATTGGGTGGGTGGGTGGGT | dA20 and d20A; &dA20-G4 and A20-G4; $dG4-A20 and dG4-20A have the same sequence.

TABLE 2-2

List of constructs of RNA/DNA heteroduplex with RNA overhang on 5' or 3'.

| Name | Sequence (X = DNA, Y = RNA, *F* = 6-FAM; \| = base-pairing) |
|---|---|
| A6 | 5' *F* ACUGUGCGUGGAAAGCGUAG<br>                    \|\|\|\|\|\|<br>3'              CGCATC |
| A8 | 5' *F* ACUGUGCGUGGAAAGCGUAG<br>                  \|\|\|\|\|\|\|\|<br>3'            TTCGCATC |
| A10 | 5' *F* ACUGUGCGUGGAAAGCGUAG<br>                \|\|\|\|\|\|\|\|\|\|<br>3'          CTTTCGCATC |
| A12 | 5' *F* ACUGUGCGUGGAAAGCGUAG<br>              \|\|\|\|\|\|\|\|\|\|\|\|<br>3'       ACCTTTCGCATC |
| A14 | 5' *F* ACUGUGCGUGGAAAGCGUAG<br>           \|\|\|\|\|\|\|\|\|\|\|\|\|\|<br>3'     GCACCTTTCGCATC |
| A16 | 5' *F* ACUGUGCGUGGAAAGCGUAG<br>        \|\|\|\|\|\|\|\|\|\|\|\|\|\|\|\|<br>3'   ACGCACCTTTCGCATC |

TABLE 2-2-continued

List of constructs of RNA/DNA heteroduplex with RNA overhang on 5' or 3'.

Sequence (X = DNA, Y = RNA, F = 6-FAM; | = base-pairing)

```
A18      5' F ACUGUGCGUGGAAAGCGUAG
              ||||||||||||||||
         3'   ACACGCACCTTTCGCATC

A20#     5' F ACUGUGCGUGGAAAGCGUAG
              ||||||||||||||||||||
         3'   TGACACGCACCTTTCGCATC

A6-      5' F ACUGUGCGUGGAAAGCGUAG
G4            ||||||
         3'             CGCATCTTGGGTGGGTGGGTGGGTT

A8-      5' F ACUGUGCGUGGAAAGCGUAG
G4            ||||||||
         3'           TTCGCATCTTGGGTGGGTGGGTGGGTT

A10-     5' F ACUGUGCGUGGAAAGCGUAG
G4            ||||||||||
         3'         CTTTCGCATCTTGGGTGGGTGGGTGGGTT

A12-     5' F ACUGUGCGUGGAAAGCGUAG
G4            ||||||||||||
         3'       ACCTTTCGCATCTTGGGTGGGTGGGTGGGTT

A14-     5' F ACUGUGCGUGGAAAGCGUAG
G4            ||||||||||||||
         3'     GCACCTTTCGCATCTTGGGTGGGTGGGTGGGTT

A16-     5' F ACUGUGCGUGGAAAGCGUAG
G4            ||||||||||||||||
         3'   ACGCACCTTTCGCATCTTGGGTGGGTGGGTGGGTT

A18-     5' F ACUGUGCGUGGAAAGCGUAG
G4            ||||||||||||||||||
         3' ACACGCACCTTTCGCATCTTGGGTGGGTGGGTGGGTT

A20-     5' F ACUGUGCGUGGAAAGCGUAG
G4&           ||||||||||||||||||||
         3' TGACACGCACCTTTCGCATCTTGGGTGGGTGGGTGGGTT

G4-      5'              F ACUGUGCGUGGAAAGCGUAG
A6                         ||||||
         3'    TTGGGTGGGTGGGTGGGTTCGCATC

G4-      5'              F ACUGUGCGUGGAAAGCGUAG
A10                        ||||||||||
         3'    TGGGTGGGTGGGTGGGTTCTTTCGCATC

G4-      5'              F ACUGUGCGUGGAAAGCGUAG
A14                        ||||||||||||||
         3'    TTGGGTGGGTGGGTGGGTTGCACCTTTCGCATC

G4-      5'              F ACUGUGCGUGGAAAGCGUAG
A18                        ||||||||||||||||||
         3'    TTGGGTGGGTGGGTGGGTTACACGCACCTTTCGCATC

G4-      5'              F ACUGUGCGUGGAAAGCGUAG
A20$                       ||||||||||||||||||||
         3'   TTGGGTGGGTGGGTGGGTTTGACACGCACCTTTCGCATC 6A       5' F ACUGUGCGUGGAAAGCGUAG
              ||||||
         3'   TGACAC 8A       5' F ACUGUGCGUGGAAAGCGUAG
              ||||||||
         3'   TGACACGC 10A      5' F ACUGUGCGUGGAAAGCGUAG
              ||||||||||
         3'   TGACACGCAC 12A      5' F ACUGUGCGUGGAAAGCGUAG
              ||||||||||||
         3'   TGACACGCACCT 14A      5' F ACUGUGCGUGGAAAGCGUAG
              ||||||||||||||
         3'   TGACACGCACCTTT 16A      5' F ACUGUGCGUGGAAAGCGUAG
              ||||||||||||||||
         3'   TGACACGCACCTTTCG 18A      5' F ACUGUGCGUGGAAAGCGUAG
              ||||||||||||||||||
         3'   TGACACGCACCTTTCGCA

20A#     5' F ACUGUGCGUGGAAAGCGUAG
              ||||||||||||||||||||
         3'   TGACACGCACCTTTCGCATC

G4-      5'              F ACUGUGCGUGGAAAGCGUAG
6A                         ||||||
         3'   TTGGGTGGGTGGGTGGGTTTGACAC

G4-      5'              F ACUGUGCGUGGAAAGCGUAG
8A                         ||||||||
         3'   TTGGGTGGGTGGGTGGGTTTGACACGC

G4-      5'              F ACUGUGCGUGGAAAGCGUAG
10A                        ||||||||||
         3'   TTGGGTGGGTGGGTGGGTTTGACACGCAC

G4-      5'              F ACUGUGCGUGGAAAGCGUAG
12A                        ||||||||||||
         3'   TTGGGTGGGTGGGTGGGTTTGACACGCACCT

G4-      5'              F ACUGUGCGUGGAAAGCGUAG
14A                        ||||||||||||||
         3'   TTGGGTGGGTGGGTGGGTTTGACACGCACCTTT

G4-      5'              F ACUGUGCGUGGAAAGCGUAG
16A                        ||||||||||||||||
         3'   TTGGGTGGGTGGGTGGGTTTGACACGCACCTTTCG

G4-      5'              F ACUGUGCGUGGAAAGCGUAG
18A                        ||||||||||||||||||
         3'   TTGGGTGGGTGGGTGGGTTTGACACGCACCTTTCGCA

G4-      5'              F ACUGUGCGUGGAAAGCGUAG
20A$                       ||||||||||||||||||||
         3'   TTGGGTGGGTGGGTGGGTTTGACACGCACCTTTCGCATC 6A-      5' F ACUGUGCGUGGAAAGCGUAG
G4            ||||||
         3'   TGACACTTGGGTGGGTGGGTGGGTT 10A-     5' F ACUGUGCGUGGAAAGCGUAG
G4            ||||||||||
         3'   TGACACGCACTTGGGTGGGTGGGTGGGTT 14A-     5' F ACUGUGCGUGGAAAGCGUAG
G4            ||||||||||||||
         3'   TGACACGCACCTTTTGGGTGGGTGGGTGGGTT 18A-     5' F ACUGUGCGUGGAAAGCGUAG
G4            ||||||||||||||||||
         3'   TGACACGCACCTTTCGCATTGGGTGGGTGGGTGGGTT 20A-     5' F ACUGUGCGUGGAAAGCGUAG
G4&           ||||||||||||||||||||
         3'   TGACACGCACCTTTCGCATCTTGGGTGGGTGGGTGGGTT
```

A20 and 20A; &A20 G4 and A20-G4; $G4-A20 and G4-20A are the same construct.

TABLE 2-3

List of RNA/DNA heteroduplex with RNA overhang on 5' and 3'.

Name | Sequence (X = DNA, Y = RNA, *F* = 6-FAM; | = base-pairing)

A8i
5' *F* ACUGUGCGUGGAAAGCGUAG
         ||||||||
3'       GCACCTTT

A10i
5' *F* ACUGUGCGUGGAAAGCGUAG
         ||||||||||
3'      CGCACCTTTC

A12i
5' *F* ACUGUGCGUGGAAAGCGUAG
         ||||||||||||
3'     ACGCACCTTTCG

A14i
5' *F* ACUGUGCGUGGAAAGCGUAG
         ||||||||||||||
3'    CACGCACCTTTCGC

A16i
5' *F* ACUGUGCGUGGAAAGCGUAG
         ||||||||||||||||
3'   ACACGCACCTTTCGCA

G4T-A8i-TTG4
5'                *F* ACUGUGCGUGGAAAGCGUAG
                        ||||||||
3'     TGGGTGGGTGGGTGGGGTTGCACCTTTTGGGTGGGTGGGTGGGTT

G4T-A10i-TTG4
5'                *F* ACUGUGCGUGGAAAGCGUAG
                        ||||||||||
3'     TGGGTGGGTGGGTGGGGTTCGCACCTTTCTGGGTGGGTGGGTGGGTT

G4T-A12i-TTG4
5'                *F* ACUGUGCGUGGAAAGCGUAG
                        ||||||||||||
3'     TGGGTGGGTGGGTGGGGTTACGCACCTTTCGTGGGTGGGTGGGTGGGTT

G4T-A14i-TTG4
5'                *F* ACUGUGCGUGGAAAGCGUAG
                        ||||||||||||||
3'     TGGGTGGGTGGGTGGGGTTCACGCACCTTTCGCTGGGTGGGTGGGTGGGTT

G4T-A16i-TTG4
5'                *F* ACUGUGCGUGGAAAGCGUAG
                        ||||||||||||||||
3'     TGGGTGGGTGGGTGGGGTTACACGCACCTTTCGCATGGGTGGGTGGGTGGGTT

G4-A8i-G4
5'                *F* ACUGUGCGUGGAAAGCGUAG
                        ||||||||
3'     TGGGTGGGTGGGTGGGGCACCTTTGGGTGGGTGGGTGGGTT

G4-A10i-G4
5'                *F* ACUGUGCGUGGAAAGCGUAG
                        ||||||||||
3'     TGGGTGGGTGGGTGGGGCGCACCTTTCGGGTGGGTGGGTGGGTT

G4-A12i-G4
5'                *F* ACUGUGCGUGGAAAGCGUAG
                        ||||||||||||
3'     TGGGTGGGTGGGTGGGGACGCACCTTTCGGGGTGGGTGGGTGGGTT

G4-A14i-G4
5'                *F* ACUGUGCGUGGAAAGCGUAG
                        ||||||||||||||
3'     MTGGGTGGGTGGGTGGGTCACGCACCTTTCGCGGGTGGGTGGGTGGGTT

G4-A16i-G4
5'                *F* ACUGUGCGUGGAAAGCGUAG
                        ||||||||||||||||
3'     TGGGTGGGTGGGTGGGGACACGCACCTTTCGCAGGGTGGGTGGGTGGGTT

G4T-A8i-TG4
5'                *F* ACUGUGCGUGGAAAGCGUAG
                        ||||||||
3'     TGGGTGGGTGGGTGGGGTGCACCTTTTGGGTGGGTGGGTGGGTT

G4T-A10i-TG4
5'                *F* ACUGUGCGUGGAAAGCGUAG
                        ||||||||||
3'     TGGGTGGGTGGGTGGGGTCGCACCTTTCTGGGTGGGTGGGTGGGTT

G4T-A12i-TG4
5'                *F* ACUGUGCGUGGAAAGCGUAG
                        ||||||||||||
3'     TGGGTGGGTGGGTGGGGTACGCACCTTTCGTGGGTGGGTGGGTGGGTT

G4T-A14i-TG4
5'                *F* ACUGUGCGUGGAAAGCGUAG
                        ||||||||||||||
3'     TGGGTGGGTGGGTGGGGTCACGCACCTTTCGCTGGGTGGGTGGGTGGGTT

TABLE 2-3-continued

List of RNA/DNA heteroduplex with RNA overhang on 5' and 3'.

Name    Sequence (X = DNA, Y = RNA, F = 6-FAM; | = base-pairing)

G4T-A16i-  5'           F ACUGUGCGUGGAAAGCGUAG
TG4                       ||||||||||||||||||||
           3' TGGGTGGGTGGGTGGGGTACACGCACCTTTCGCATGGGTGGGTGGGTGGGTT

G4TT-A8i-  5'           F ACUGUGCGUGGAAAGCGUAG
TTG4                         ||||||||
           3'  TGGGTGGGTGGGTGGGGTTGCACCTTTTTGGGTGGGTGGGTGGGTT

G4TT-     5'            F ACUGUGCGUGGAAAGCGUAG
A10i-TTG4                   ||||||||||
           3'  TGGGTGGGTGGGTGGGGTTCGCACCTTTCTTGGGTGGGTGGGTGGGTT

G4TT-     5'            F ACUGUGCGUGGAAAGCGUAG
A12i-TTG4                  ||||||||||||
           3'  TGGGTGGGTGGGTGGGGTTACGCACCTTTCGTTGGGTGGGTGGGTGGGTT

G4TT-     5'            F ACUGUGCGUGGAAAGCGUAG
A14i-TTG4                 ||||||||||||||
           3'  TGGGTGGGTGGGTGGGGTTCACGCACCTTTCGCTTGGGTGGGTGGGTGGGTT

G4TT-     5'            F ACUGUGCGUGGAAAGCGUAG
A16i-TTG4                ||||||||||||||||
           3'  TGGGTGGGTGGGTGGGGTTACACGCACCTTTCGCATTGGGTGGGTGGGTGGGTT

Example 3: Enhanced Gene Knockdown Activity with Lipid-Conjugated SEA Oligo

Measurement of cellular uptake of oligo by flow cytometry. HeLa cells were seeded (100,000 cells per well) onto 12-well plates 24 h prior to experiment in complete DMEM media at 37° C. and 5% $CO_2$. Cells were incubated in complete media containing FAM-labeled oligonucleotides at a final concentration of 0.1 μM for 1, 5, 9, or 24 h at 37° C. At the set time points, the growth medium was removed and cells were washed twice with PBS (500 μL) and harvested by scrapping. Cell suspension in PBS (500 μL) was transferred into 5 mL round bottom tubes. Cells were fixed with freshly made 4% (w/v) paraformaldehyde for 10 min. After fixing, cells were washed twice by centrifugation at 130×g for 10 min in PBS (1 mL) and resuspended with PBS (500 μL) for flow cytometry (BD FACSCalibur). For each sample, 10,000 events were collected in a selected gate that corresponds to the untreated single cell population. FITC fluorescence was measured by air-cooled argon laser at 488-nm. Flowjo software was used to analyze the gated shift in histograms with FITC for cells treated with different FAM-labeled oligonucleotides with reference to the untreated cell populations. All data were collected as duplicates and shown as mean±standard deviation.

Figure 5:
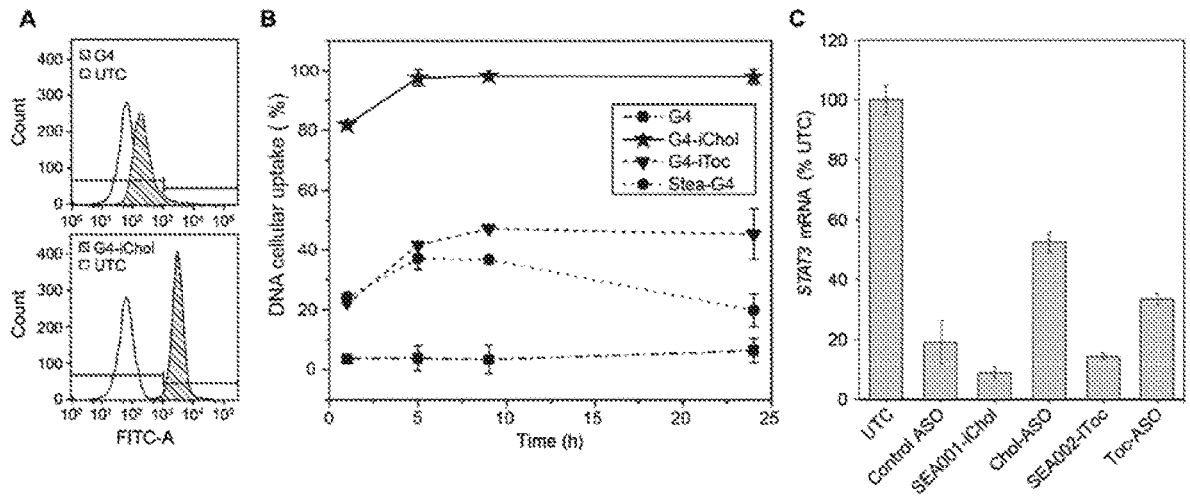
FIG. 5 shows enhanced cellular uptake of G-quadruplex structures that are conjugated with lipids and lipid-soluble moieties. A) Comparative fluorescence-activated cells sorting (FACS) analysis of uptake of oligonucleotides by HeLa cells at 24 h—top: G4; bottom: G4 with internal cholesterol modifier (G4-iChol), untreated control (UTC). B) Time course of oligonucleotide uptake by HeLa cells at 37° C. Oligonucleotides screened are G4 (square), G4 with internal cholesterol modifier (G4-iChol, star), G4 with internal tocopherol modifier (G4-iToc, triangle) and G4 with 5' stearyl modifier (Stea-G4, circle). C) Measurement of STAT3 gene knockdown in HeLa cells following 24 h treatment with 10 nM of the respective oligonucleotides pre-mixed in Lipofectamine® RNAiMAX.

G-quadruplex structures conjugated with lipids and lipid-soluble moieties at either the 5'-terminus (stearate) or the loop (cholesterol and α-tocopherol) show enhanced uptake by HeLa cells (FIG. 5).

TABLE 3-1

Table of constructs used in the lipid-conjugated SEA oligo study.

| Name | Study | SEQ ID NO: | Sequence (5' to 3'; X = DNA; X = LNA; Chol = Cholesterol modifier; Toc = Tocopherol modifier; Stea = Stearyl modifier; SS = disulfide linker; * = phosphorothioate bond; F = 6-FAM) |
|---|---|---|---|
| G4 | Cells uptake | 82 | TTGGGTGGGTGGGTGGGT F |
| G4-iChol | Cells uptake | 83 | TTGGGTGGG Toc TGGGTGGGT F |
| G4-iToc | Cells uptake | 84 | TTGGGTGGG Chol TGGGTGGGT F |
| Stea-G4 | Cells uptake | 85 | Stea TTGGGTGGGTGGGTGGGT F |
| Control ASO# | Gene knockdown | 86 | **C*T*A*T*T*T*G*G*A*T*G*T*C*A*G*C** |
| Chol-ASO | Gene knockdown | 87 | Chol **C*T*A*T*T*T*G*G*A*T*G*T*C*A*G*C** |

TABLE 3-1-continued

Table of constructs used in the
lipid-conjugated SEA oligo study.

| Name | Study | SEQ ID NO: | Sequence (5' to 3'; X = DNA; X = LNA; Chol = Cholesterol modifier; *Toc* = Tocopherol modifier; *Stea* = Stearyl modifier; *SS* = disulfide linker; * = phosphorothioate bond; F = 6-FAM) |
|---|---|---|---|
| Toc-ASO | Gene knockdown | 88 | *Toc* C\*T\*A\*T\*T\*T\*G\*G\*A\*T\*G\*T\*C\*A\*G\*C |
| SEA001-iChol | Gene knockdown | 89 | TTGGGTGGG *Chol* TGGGTGGGT *SS* C\*T\*A\*T\*T\*T\*G\*G\*A\*T\*G\*T\*C\*A\*G\*C |
| SEA002-iToc | Gene knockdown | 90 | TTGGGTGGG *Toc* TGGGTGGGT *SS* C\*T\*A\*T\*T\*T\*G\*G\*A\*T\*G\*T\*C\*A\*G\*C |

Control ASO is the LNA version of a clinical phase 2 gapmer, AZD9150.

Example 4: Enhanced Gene Knockdown Activity with Peptide-Conjugated SEA Oligo Preparation of peptide-conjugated oligonucleotides. 3-nitro-2-pyridine sulfenyl (NPys)-modified peptide (5 equiv) was added to a solution mixture of thiol-modified oligonucleotide (1 equiv) in H$_2$O (3.15 μL/nmol), formamide (4.3 μL/nmol) and 2M TEAA (0.6 μL/nmol). The reaction mixture was vortexed, centrifuged and kept at room temperature for 3 h, with the process of vortex and centrifugation repeated every hour. The reaction mixture was filtered with micro spin filter (pore size 0.2 μm, nylon) prior to purification with RP-UHPLC (column, YMC-Triact C18, 120 Å, 4.6×250 mm; Buffer A, 0.1 M TEAA; Buffer B, MeCN; flow rate: 1.0 mL/min).

Cell transfection study of ASO, peptide-conjugated ASO, and peptide-conjugated SEA oligo. HeLa cells were seeded in 12-well plates (TPP®) at 25% confluency in complete DMEM media containing 10% FBS (Gibco®) 24 h prior to ASO treatment. ASO, peptide-ASO conjugate, and peptide-G4-ASO conjugates were pre-mixed with Lipofectamine RNAiMAX according to the manufacturer's protocol and added to the cell culture media to a final concentration of 10 nM for a further incubation of 24 h. Total RNA was isolated by TRIzol reagent (Invitrogen) according to the manufacturer's protocol. One microgram of total RNA per sample was reverse transcribed to cDNA using M-MLV reverse transcriptase (Promega) and random hexamer/oligo-dT primers. One fiftieth of the resulting reactions were used for quantitative PCR (qPCR) with primer pairs for STAT3 (Forward: 5'-ACATGCCACTTTGGTGTTTCATAA-3' (SEQ ID NO: 91); Reverse: 5'-TCTTCGTAGATTGTGCTGATAGAGAAC-3' (SEQ ID NO: 92)) and β-actin (Forward: 5'-CGGACTATGACTTAGTTGCGTTACA-3' (SEQ ID NO: 93); Reverse: 5'-GCCATGCCAATCTCATCTTGT-3'(SEQ ID NO: 94)). The qPCR reactions were performed for 40 cycles of annealing at 55° C. for 10 s, extension at 72° C. for 20 s, and denaturation at 95° C. for 10 s.

The mRNA level was normalized using the endogenous β-actin (ACTB) mRNA as an internal control. Relative STAT3 mRNA levels were determined from the calculated threshold cycle (Cq) by the LightCycler®480 CW 1.5.1 software and compared to untreated controls (UTC) using ΔΔCq calculation method. Each sample was analyzed in duplicate.

Figure 6:
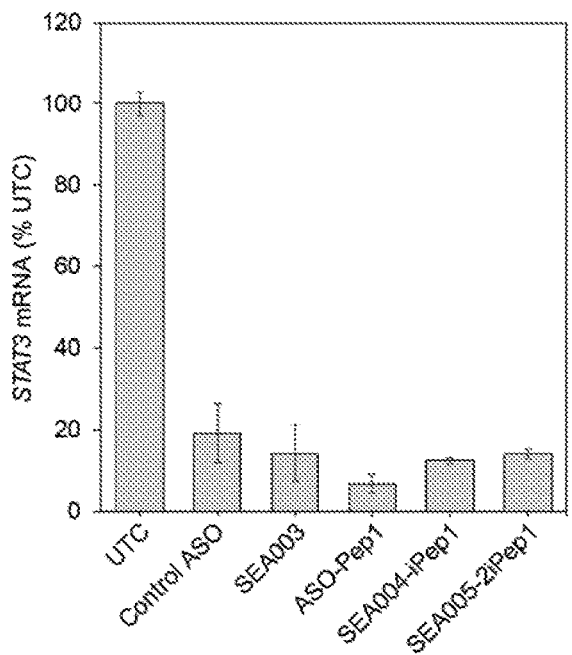
FIG. 6 shows STAT3 gene knockdown by control ASO gapmer, G4-conjugated ASO gapmer (SEA003), peptide (GFWFG)-conjugated ASO gapmer (ASO-Pep1), single (SEA004-iPep1) and double (SEA005-2iPep1) peptide (GFWFG)-conjugated SEA oligo. HeLa cells were transfected with 10 nM of the respective oligonucleotides pre-mixed in Lipofectamine® RNAiMAX.

STAT3 gene knockdown by ASO gapmer, SEA oligo, peptide-conjugated ASO gapmer, and peptide-conjugated SEA oligo in HeLa cells are shown in FIG. 6. The ASO gapmer utilized is the LNA equivalent of AZD9150 (U.S. Pat. No. 9,359,608 B2; Hong et al., Sci. Transl. Med. 2015, 7, 314ra185). The peptide employed (GFWFG) was previously shown to promote endosomal escape enhancement (LOnn et al., *Sci. Rep.* 2016, 6, 32301) of biomacromolecules.

TABLE 4-1

Table of constructs used in the
peptide-conjugated SEA Oligo study.

| Name | Study | SEQ ID NO: | Sequence (5' to 3'; X = DNA; X = LNA; Pep1 = GFWFG peptide; *Pep1-T* = GFWFG peptide conjugated on dT; SS = disulfide linker; * = phosphorothioate bond) |
|---|---|---|---|
| Control ASO# | Gene knock down | 86 | C\*T\*A\*T\*T\*T\*G\*G\*A\*T\*G\*T\*C\*A\*G\*C |
| SEA003 | Gene knock down | 95 | TTGGGTGGGTGGGTGGGT *SS* C\*T\*A\*T\*T\*T\*G\*G\*A\*T\*G\*T\*C\*A\*G\*C |
| ASO-Pep1 | Gene knock down | 96 | C\*T\*A\*T\*T\*T\*G\*G\*A\*T\*G\*T\*C\*A\*G\*C *SS Pep1* |
| SEA004-iPep1 | Gene knock down | 97 | TTGGGTGGG *Pep1-T* GGGTGGGT SS C\*T\*A\*T\*T\*T\*G\*G\*A\*T\*G\*T\*C\*A\*G\*C |
| SEA005-2iPep1 | Gene knock down | 98 | TTGGG *Pep1-T* GGGTGGG *Pep1-T* GGGT *SS* C\*T\*A\*T\*T\*T\*G\*G\*A\*T\*G\*T\*C\*A\*G\*C |

Control ASO is the LNA version of a clinical phase 2 gapmer, AZD9150.

Example 5: GalNAc-Conjugated G-Quadruplex and SEA Oligo

Preparation of mono- and poly-GalNAc-conjugated G-quadruplex. GalNAc-conjugated guanine phosphoramidite was synthesized according to procedures by Manoharan, M. et. al. (U.S. Pat. No. 2016/0376585 A1) and incorporated onto oligonucleotides via an automated DNA synthesizer using standard solid-phase oligonucleotide synthesis. The GalNAc-containing oligonucleotides were treated 1 M 1,8-Diazabicyclo[5.4.0]undec-7-ene in anhydrous acetonitrile prior to deprotection with concentrated ammonium hydroxide, and purified by RP-UHPLC (column, YMC-Triact C18, 120 Å, 4.6×250 mm; Buffer A, 0.1 M TEAA; Buffer B, MeCN; flow rate: 1.0 mL/min). The samples were dialyzed successively against 2 mM KCl and water, lyophilized and resuspended in buffer containing 10 mM KPi, 10% $D_2O$, pH 7.0 prior to characterization by NMR spectroscopy.

Single or multiple ligands can be conjugated onto the G-tetrad core or loops of the G-quadruplex structure in multiple combinations (FIG. 7-I). Here we demonstrated the conjugation of mono-(FIG. 7-IIB,C), di-(FIG. 7-IID), and tri-(FIG. 7-IIE) GalNAc units onto the G-tetrad core.

Conjugation of multiple GalNAc units onto ASO (U.S. Pat. Nos. 9,181,549 B2, 9,249,179 B2, 9,370,582 B2, 2015/0368642 A1; Sliedregt et al., *J. Med. Chem.* 1999, 42, 609; Rozema et al., *Proc. Natl. Acad. Sci. USA* 2007, 104, 12982; Khorev et al., *Bioorg. Med. Chem.* 2008, 16, 5216; Prakash et al., *Nucleic Acids Res.* 2014, 42, 8796; Nair et al., *J. Am. Chem. Soc.* 2014, 136, 16958; Matsuda et al., *ACS Chem. Biol.* 2015, 10, 1181; Rajeev et al., *Chembiochem* 2015, 16, 903) was previously shown to lead to enhanced delivery to liver hepatocytes, resulting in highly effective gene knockdown of liver targets involved in lipid metabolism (e.g. APOB (U.S. Pat. No. 8,735,364 B2; Straarup et al., *Nucleic Acids Res.* 2010, 38, 7100), PCSK9 (U.S. Pat. No. 8,912,160 B2), APOC3 (U.S. Pat. No. 9,163,239 B2), LPA (U.S. Pat. No. 9,181,550 B2), and ANGPTL3(U.S. Pat. No. 9,139,831 B2)).

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. Other embodiments are within the following claims.

One skilled in the art would readily appreciate that the present invention is well adapted to carry out the objects and obtain the ends and advantages mentioned, as well as those inherent therein. Further, it will be readily apparent to one skilled in the art that varying substitutions and modifications may be made to the invention disclosed herein without departing from the scope and spirit of the invention. The compositions, methods, procedures, treatments, molecules and specific compounds described herein are presently representative of preferred embodiments are exemplary and are not intended as limitations on the scope of the invention. Changes therein and other uses will occur to those skilled in the art which are encompassed within the spirit of the invention are defined by the scope of the claims. The listing or discussion of a previously published document in this specification should not necessarily be taken as an acknowledgement that the document is part of the state of the art or is common general knowledge.

The invention illustratively described herein may suitably be practiced in the absence of any element or elements, limitation or limitations, not specifically disclosed herein. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by exemplary embodiments and optional features, modification and variation of the inventions embodied therein herein disclosed may be resorted to by those skilled in the art, and that such modifications and variations are considered to be within the scope of this invention.

The content of all documents and patent documents cited herein is incorporated by reference in their entirety.

The disclosures of the following documents are hereby incorporated into the present application by reference in their entirety:

| PATENT DOCUMENTS | | |
|---|---|---|
| Gapmer: | | |
| U.S. Pat. No. 6,326,199 B1 | December 2001 | Cook et al. |
| U.S. Pat. No. 7,015,315 B1 | March 2006 | Cook et al. |
| U.S. Pat. No. 8,703,728 B2 | April 2014 | Swayze et al. |
| U.S. Pat. No. 9,045,754 B2 | June 2015 | Bhanot et al. |
| End-stabilizing oligo: | | |
| 2015/0050738 A1 | | Ozsolak et al. |
| GalNAc conjugation: | | |
| U.S. Pat. No. 9,181,549 B2 | November 2015 | Prakash et al. |
| U.S. Pat. No. 9,249,179 B2 | February 2016 | Hadwiger et al. |
| U.S. Pat. No. 9,370,582 B2 | June 2016 | Manoharan et al. |
| US 2015/0368642 A1 | December 2015 | Albæk et al. |
| US 2016/0376585 A1 | December 2016 | Manoharan et al. |
| STAT3: | | |
| U.S. Pat. No. 9,359,608 B2 | June 2016 | Swayze et al. |
| APOB: | | |
| U.S. Pat. No. 8,735,364 B2 | January 2008 | Crooke and Graham |
| PCSK9: | | |
| U.S. Pat. No. 8,912,160 B2 | December 2014 | Freier et al. |
| APOC3: | | |
| U.S. Pat. No. 9,163,239 B2 | October 2015 | Prakash et al. |
| LPA: | | |
| U.S. Pat. No. 9,181,550 B2 | November 2015 | Prakash et al. |
| ANGPTL3: | | |
| U.S. Pat. No. 9,139,831 B2 | September 2015 | Crooke et al. |
| Modified G-quadruplex nanoparticles: | | |
| US 2016/0310519 A1 | October 2016 | Phan et al. |
| LNA: | | |
| WO1999014226 A2 | March 1999 | Wengel and Nielsen |
| WO2000066604 A2 | November 2000 | Wengel J |
| WO2003095467 A1 | November 2003 | Sorensen et al. |
| cEt: | | |
| WO2012109395 A1 | August 2012 | Freier and Swayze |

OTHER PUBLICATIONS

Oligotherapeutics:
Sharma et al., *Fut. Med. Chem.* 2015, 7, 2221
ASO:
Zamecnik et al., *Proc. Natl. Acad. Sci. USA* 1978, 75, 280
Stephenson et al., *Proc. Natl. Acad. Sci. USA* 1978, 75, 285
Crooke et al., *Nucleic Acid Ther.* 2017, 27, 70
Crooke et al., *Nat. Biotechnol.* 2017, 35, 230
Bennett et al., *Annu. Rev. Pharmacol. Toxicol.* 2017, 57, 81
Phosphorothioate:
Eckstein F., *J. Am. Chem. Soc.* 1966, 88, 4292
Gapmer:
Monia et al., *Biochemistry* 1993, 268, 14514
LNA:
Obika et al., *Tetrahedron Lett.* 1997, 38, 8735
Koshkin et al., *Tetrahedron* 1998, 54, 3607 cEt:
Seth et al., *J. Med. Chem.* 2009, 52, 10
Automated synthesis of oligo:
Matteucci and Caruthers, *J. Am. Chem. Soc.* 1981, 103, 3185
GalNAc conjugation:
Sliedregt et al., *J. Med. Chem.* 1999, 42, 609
Rozema et al., *Proc. Natl. Acad. Sci. U.S.A.* 2007, 104, 12982
Khorev et al., *Bioorg. Med. Chem.* 2008, 16, 5216
Prakash et al., *Nucleic Acids Res.* 2014, 42, 8796
Nair et al., *J. Am. Chem. Soc.* 2014, 136, 16958

Matsuda et al., *ACS Chem. Biol.* 2015, 10, 1181
Rajeev et al., *Chembiochem* 2015, 16, 903
STAT3:
Hong et al., *Sci. Transl. Med.* 2015, 7, 314ra185
APOB:
Straarup et al., *Nucleic Acids Res.* 2010, 38, 7100
Endosomal escape enhancement peptide:
LÖnn et al., *Sci. Rep.* 2016, 6, 32301
G-quadruplex:
Phan A. T., *FEBS J.* 2010, 277, 1107

What is claimed is:

1. A conjugate consisting of:
   (1)(a) an antisense oligonucleotide (ASO), wherein the ASO is at least 5 nucleotides in length and (b) at least one G-quadruplex structure, or
   (2)(a) an antisense oligonucleotide (ASO), wherein the ASO is at least 5 nucleotides in length, (b) at least one G-quadruplex structure, and (c) a linker connecting the at least one G-quadruplex structure to the ASO, or
   (3)(a) an antisense oligonucleotide (ASO), wherein the ASO is at least 5 nucleotides in length, (b) at least one G-quadruplex structure, and (d) single or multiple ligands or functional moieties conjugated to the at least one G-quadruplex structure, or
   (4)(a) an antisense oligonucleotide (ASO), wherein the ASO is at least 5 nucleotides in length, (b) at least one G-quadruplex structure, (c) a linker connecting the at least one G-quadruplex structure to the ASO, and (d) single or multiple ligands or functional moieties conjugated to the at least one G-quadruplex structure,
   wherein the ASO and the at least one G-quadruplex structure are heterologous to each other, and wherein the conjugate has increased nuclease resistance relative to the unconjugated ASO.

2. The conjugate of claim 1, wherein the ASO is chemically modified.

3. The conjugate of claim 1, wherein the ASO adopts a gapmer design or a mixmer design.

4. The conjugate of claim 1, wherein the conjugate comprises (a) one G-quadruplex structure 5' to the ASO, (b) one G-quadruplex structure 3' to the ASO, or (c) both.

5. The conjugate of claim 1, wherein the at least one G-quadruplex structure comprises
   (a) a nucleic acid molecule comprising the nucleic acid sequence $(g)_w(n)_a(g)_x(n)_b(g)_y(n)_c(g)_z$, wherein g and n are natural or chemical analogues of guanine nucleobase and any nucleobase respectively, w, x, y, z are independently of each other integers of at least 0, a, b, c are independently of each other integers of at least 0, and the sum of integers w, x, y, z is at least 8;
   (b) four nucleic acid molecules wherein each of said molecules comprises a sequence of $(g)_z$, wherein z is an integer of at least 2; or
   (c) two nucleic acid molecules wherein each of said molecules comprises a sequence of $(g)_y(n)_b(g)_z$, wherein b is an integer of at least 0, y and z are independently of each other integers of at least 0, and the sum of integers y and z is at least 4.

6. The conjugate according to claim 5, wherein the nucleic acid molecule comprises the nucleic acid sequence $(g)_w(n)_a(g)_x(n)_b(g)_y(n)_c(g)_z$ wherein g and n are natural or chemical analogues of guanine nucleobase and any nucleobase respectively, w, x, y, z are independently of each other integers of at least 3 and a, b, c are independently of each other integers of at least 1.

7. The conjugate of claim 1, wherein the at least one G-quadruplex structure is chemically modified.

8. The conjugate of claim 1, wherein loops of the at least one G-quadruplex structure comprise non-nucleosidic analogues without a base.

9. The conjugate of claim 1, wherein the linker is composed of unmodified nucleotides or wherein the linker is composed of chemically modified nucleotides, in part or in full.

10. The conjugate of claim 1, wherein the linker comprises a reducible linkage, an acid-labile linkage, or a protease-labile linkage.

11. The conjugate of claim 1, wherein the linker is connected to a phosphate or phosphate analogue, sugar, or base on the G-tetrad core or loop of the at least one G-quadruplex structure.

12. The conjugate of claim 1, wherein the linker is connected to a phosphate or phosphate analogue, sugar, or base on the ASO.

13. The conjugate of claim 1, wherein the at least one G-quadruplex structure and the ASO are connected across the backbone, in the form of a contiguous nucleotide sequence.

14. The conjugate of claim 1, wherein the ligand or functional moiety is selected from the group consisting of small molecules, carbohydrates, vitamins, lipids, aptamers, peptides, proteins, antibodies, fluorescent labels, and radiolabel tracers.

15. The conjugate of claim 1, wherein the ligand or functional moiety is connected to a phosphate or phosphate analogue, sugar, base or non-nucleosidic analogue on the G-tetrad core or loop of the at least one G-quadruplex structure.

16. The conjugate of claim 1, wherein the ASO is complementary to a portion of a DNA, pre-mRNA, mRNA, regulatory RNA, or non-coding RNA.

17. A method for preventing or treating diseases, disorders, and conditions, comprising administering a therapeutically effective amount of the conjugate of claim 1 to a subject in need thereof.

18. A method of modulating the stability, translation, splicing, cleavage, or activity of a target nucleic acid molecule, comprising contacting the target nucleic acid molecule with a conjugate of claim 1 having an ASO complementary to a portion of the target nucleic acid molecule.

19. A method of imaging or diagnosing, the method comprising contacting a selective probe with a target nucleic acid molecule, wherein the selective probe comprises a conjugate of claim 1.

* * * * *